(12) United States Patent
Lin et al.

(45) Date of Patent: Sep. 30, 2025
(10) Patent No.: US 12,426,825 B2

(54) GRADING METHOD OF PHYSIOLOGICAL AND EMOTIONAL RESPONSE OF ELECTROENCEPHALOGRAPH (EEG)

(71) Applicants: StrongLED Smart Lighting (Cayman) Co., Ltd., Grand Cayman (KY); Lawrence Lin, Taoyuan (TW)

(72) Inventors: Lawrence Lin, Taoyuan (TW); Chih Hung Chang, New Taipei (TW)

(73) Assignees: STRONGLED SMART LIGHTING (CAYMAN) CO., LTD., Grand Cayman (KY); Lawrence Lin, Taoyuan (TW)

( * ) Notice: Subject to any disclaimer, the term of this patent is extended or adjusted under 35 U.S.C. 154(b) by 609 days.

(21) Appl. No.: 17/712,606

(22) Filed: Apr. 4, 2022

(65) Prior Publication Data

US 2022/0373985 A1    Nov. 24, 2022

Related U.S. Application Data

(60) Provisional application No. 63/190,426, filed on May 19, 2021.

(51) Int. Cl.
A61B 5/347 (2021.01)
A61B 5/055 (2006.01)
(Continued)

(52) U.S. Cl.
CPC ............. *A61B 5/374* (2021.01); *A61B 5/055* (2013.01); *A61B 5/165* (2013.01); *A61B 5/372* (2021.01);
(Continued)

(58) Field of Classification Search
CPC ........................... G06F 2203/011; G06F 3/015
See application file for complete search history.

(56) References Cited

U.S. PATENT DOCUMENTS

2002/0007105 A1* 1/2002 Prabhu ................. A61M 21/00
600/26

FOREIGN PATENT DOCUMENTS

| KR | 20130022887 A | * | 3/2013 |
| KR | 20130096399 A | * | 8/2013 |
| KR | 20170090590 A | * | 8/2017 |

OTHER PUBLICATIONS

Park et al., "Effects of Color Temperature and Brightness on Electroencephalogram Alpha Activity in a Polychromatic Light-emitting Diode," 2013, Clinical Psychopharmacology and Neuroscience, 11(3), pp. 126-131. (Year: 2013).*

(Continued)

*Primary Examiner* — Jon Eric C Morales
(74) *Attorney, Agent, or Firm* — MUNCY, GEISSLER, OLDS & LOWE, P.C.

(57) ABSTRACT

The present invention is grading method for establishing the response of EEG files to physiological emotions through human factor lighting (HCL) system and EEG includes the following steps: Step 1, enhance spectrum which obtained the specific color temperature with synergistic effect on the specific physiological emotional response identified by fMRI; Step 2, making the user wear an EEG and give the element with specific emotional stimulation to stimulate the user's specific physiological emotion and induced the user's specific physiological emotion; Step 3, carry out the lighting program, after step 2, start the HCL system to lighting the user with different color temperatures, record and store the EEG files after lighting with different color temperatures; Step 4, EEG files that classify specific emotions by similarity through the learning method of AI; Step 5, establish the EEG classification database according to the similarity ranking of EEG files with specific color temperature.

4 Claims, 11 Drawing Sheets

(51) Int. Cl.
  *A61B 5/16* (2006.01)
  *A61B 5/372* (2021.01)
  *A61B 5/374* (2021.01)
  *A61B 5/378* (2021.01)
  *G05B 19/042* (2006.01)
  *G06F 3/01* (2006.01)
  *G06T 15/50* (2011.01)
  *G06T 19/00* (2011.01)
  *H05B 47/155* (2020.01)
  *H05B 47/19* (2020.01)
  *A61B 5/00* (2006.01)
  *A61M 21/00* (2006.01)
  *H05B 47/105* (2020.01)

(52) U.S. Cl.
  CPC ............ *A61B 5/378* (2021.01); *G05B 19/042* (2013.01); *G06F 3/015* (2013.01); *G06T 15/50* (2013.01); *G06T 19/006* (2013.01); *H05B 47/155* (2020.01); *H05B 47/19* (2020.01); *A61B 5/7246* (2013.01); *A61M 2021/0044* (2013.01); *G05B 2219/25011* (2013.01); *G06F 2203/011* (2013.01); *H05B 47/105* (2020.01)

(56) References Cited

OTHER PUBLICATIONS

Zhang et al., "Effect of Indoors Artificial Lighting Conditions on Computer-Based Learning Performance," 2020, Int. J. Environ. Res. Public Health, 17, pp. 1-11. (Year: 2020).*

* cited by examiner

GRADING METHOD OF PHYSIOLOGICAL AND EMOTIONAL RESPONSE OF ELECTROENCEPHALOGRAPH (EEG)

CROSS-REFERENCE TO RELATED APPLICATIONS

This application claims the benefit of U.S. 63/190,426, filed May 19, 2021, which is incorporated in its entirety by reference herein.

FIELD OF THE INVENTION

The present invention relates to a grading method of electroencephalograph (EEG) for physiological and emotional response, in particular to a grading method for establishing electroencephalogram file for physiological and emotional response through Human Centric Lighting (HCL) system and EEG.

BACKGROUND OF THE INVENTION

Humans are animals with changeable emotions, they will have different emotional reactions with the individual's psychological state, such as excitement, amusement, anger, disgust, fear, happiness, sadness, serene, neutral. When negative emotions (such as anger, disgust and fear) cannot be resolved in time, they will cause psychological damage or trauma to the human body, and finally evolve into mental illness. Therefore, how to timely provide an emotional resolution or relief or treatment system that can meet the needs of users has broad business opportunities in today's society, full of high competition and high pressure at any time.

In modern medical equipment, the changes of hemodynamics caused by neuronal activity can be measured by functional Magnetic Resonance Imaging (fMRI) system. Due to the non-invasiveness of fMRI and its low radiation exposure, fMRI is currently mainly used in the study of human and animal brain or spinal cord. At the same time, the tester can also be checked by the electroencephalogram of the EEG, and the emotions can be stimulated in the same way, and the responses of different emotions can be seen, for example, the brainwave patterns of fear and happiness can be seen significantly different. Among them, when observing the response of a certain emotion under fMRI and electroencephalograph (EEG), for example, under happy emotion (which can be induced by pictures and matched with facial emotion recognition), fMRI was used to observe the blood oxygen-level dependent (BOLD) contrast response and found that in the Medial prefrontal cortex (Mpfc), there were significantly more responses to the corresponding emotions (anger and fear). In contrast, for example, in the case of fear and anger, fMRI was used to observe the blood oxygen-level dependent (BOLD) contrast response, and it was found that it was significantly reflected in the amygdala region, showing that the two kinds of emotions have different response regions in the brain. Therefore, the blood oxygen-level dependent (BOLD) contrast response of different regions in the brain can be used to clearly determine which emotion the tester is currently in. In addition, if the electroencephalogram of the EEG is used to examine the measurement tester, and the emotions are stimulated in the same way, it can be seen that the brainwave patterns of fear and happiness are significantly different. Therefore, you can also judge what kind of emotion the tester is currently in through the brainwave patterns of different reactions. According to the above, for the functional Magnetic Resonance Imaging (fMRI) system, emotions are distinguished by different blood oxygen-level dependent (BOLD) contrast reactions, while for the electroencephalograph (EEG), emotions are distinguished by different brainwave patterns. It is obvious that the methods used to judge the emotion of the tester and the contents recorded are completely different. Therefore, in terms of current science and technology, the brainwave patterns of electroencephalograph (EEG) cannot replace the blood oxygen-level dependent (BOLD) contrast response of functional Magnetic Resonance Imaging (fMRI) for the test results of the same emotion of the same tester.

The above discussion on emotion judgment by functional Magnetic Resonance Imaging (fMRI) system and electroencephalograph (EEG) is that fMRI system is very expensive and huge, so it cannot be used in commercial systems and methods of human centric lighting. Similarly, if only the brainwave patterns of the electroencephalograph (EEG) are used to judge the mood of the tester, it may be encountered that the brainwave patterns of different testers for different emotions may be different. Therefore, at present, it is impossible to use the blood oxygen-level dependent (BOLD) contrast response of functional magnetic resonance imaging (fMRI) system alone, or the brain wave mode of electroencephalograph (EEG) alone to construct a commercial human centric lighting method and system through the editing of spectral recipe.

SUMMARY OF THE INVENTION

According to the above description, the present invention provides a method to establish a correlation between the brainwave pattern of an electroencephalograph (EEG) and the blood oxygen-level dependent (BOLD) contrast of a functional Magnetic Resonance Imaging (fMRI), after which the brainwave pattern of an electroencephalograph (EEG) is used as a human centric lighting application on a commercial system.

The invention provides an electroencephalograph grading method of physiological and emotional response, which is to establish a grading method of physiological and emotional response by means of an intelligent human centric lighting system and an electroencephalogram file and includes the following steps, obtained, enhanced spectrum of different emotions, enhanced spectrum for different emotions is obtained, where the enhanced spectrum is a specific color temperature that has a synergistic effect on a specific physiological and emotional response identified by fMRI. Inducing users' specific physiological emotion is to let users wear EEG and give elements with specific emotional stimulation to stimulate users' specific physiological emotion, the lighting program is to activate the intelligent human centric lighting system to lighting the tester with different color temperatures after inducing the user's specific physiological emotion, record and store the electroencephalogram files of the specific emotions after being illuminated with different color temperatures. Classifying the electroencephalogram file of a specific emotion is to classify the electroencephalogram file of a specific emotion by the similarity between the enhanced spectrum of the specific color temperature and the electroencephalogram file of the specific emotion through the learning method of artificial intelligence, and establishing an electroencephalogram grading database, which is to establish an electroencephalogram grading database according to the similarity ranking of various specific color temperature electroencephalogram files.

The invention also provides a grading method for the physiological and emotional response of electroencephalogram files, which is a grading method for the physiological and emotional response of electroencephalogram files established through cloud, intelligent human centric lighting system and EEG, wherein it comprises the following steps, the enhanced spectrum of different emotions is a specific color temperature that has a synergistic effect on the specific physiological and emotional response identified by fMRI. To induce the specific physiological emotion of the user is to let the user wear an EEG and give the element with specific emotional stimulation to stimulate the user with a specific physiological emotion. The lighting program is to activate the intelligent human centric lighting system to illuminate the user with different color temperatures after inducing the specific physiological emotion of the user, and record and store the electroencephalogram files of the specific emotions after being illuminated with different color temperatures. The establishment of an electroencephalogram classification and grading database is to classify the electroencephalogram files of a specific emotion based on the similarity between the enhanced spectrum of specific color temperature and the electroencephalogram files of specific emotions through the learning method of artificial intelligence, establish an electroencephalogram grading database, and build the electroencephalogram grading database in the memory module in the cloud, and judging whether the lighting parameters of specific emotions are effective is to grade the scores in the electroencephalogram grading database through the cloud, and take the grade of the scores as the judgment benchmark. If the score of the user's electroencephalogram classification reaches the benchmark after inducing the user's specific physiological emotion and starting the intelligent human centric lighting system to lighting the user with a specific color temperature, it represents that the congestion response in the user's brain is enough, then the lighting parameters of the specific color temperature at this time are stored.

The present invention further provides a method for constructing a light environment platform, also as a sharing platform, comprising the following steps, obtaining the lighting parameters of the multispectral light-emitting device is to obtain one or more lighting parameters of specific color temperature from a database. Each specific color temperature is a lighting parameter that enables a specific emotion to have a synergistic stimulation effect. The lighting parameters are used as the control parameters for the multispectral emission of the multispectral light-emitting device, and the lighting parameters are stored in the cloud environment module of the cloud. The construction of the spectral recipe database is to store the light scene data with the lighting parameters providing specific color temperature into the cloud environment module according to the lighting parameters to form the spectral recipe database, and take the corresponding lighting parameters of each spectral recipe as the control parameters of the multispectral light-emitting device to emit multi spectra, and the establishment of light environment platform is to store the lighting parameters of spectral recipe into the cloud environment module in the cloud. The sharing platform is used to provide users with the lighting program for users by selecting the light scene and using the lighting parameters of each spectral recipe as the control parameters of the multispectral light-emitting device to emit multi spectra.

The present invention further provides a method for constructing a light environment platform, comprising the following steps, obtaining the lighting parameters of the multispectral light-emitting device is to obtain one or more lighting parameters of specific color temperature from a database. Each specific color temperature is a lighting parameter that enables a specific emotion to have a synergistic stimulation effect and store the lighting parameters in the cloud environment module of the cloud. The construction of spectral recipe database is to store the light scene data with lighting parameters providing specific color temperature into the cloud environment module, according to the lighting parameters to form a spectral recipe database and take the corresponding lighting parameters of each spectral recipe as a default value of lighting. The lighting program is to illuminate the user according to the default value of the corresponding lighting parameters of the spectral recipe selected by the user as the control parameter of the multispectral light-emitting device to emit multi spectra. Judging whether the lighting of the default value is effective, when the user completes the lighting program, if the user thinks that the effect of specific emotional stimulation has been achieved, the spectral recipe of specific color temperature and the lighting parameters are stored and establishing a light environment platform, which stores the lighting parameters of the spectral recipe into the public cloud on the cloud to establish a light environment platform.

The invention also provides a sharing platform that uses an intelligent human centric lighting system as a human centric lighting. The sharing platform includes: the intelligent human centric lighting system includes a cloud, and lighting field terminal and a client terminal, and the cloud, a lighting field terminal and a client terminal communicate with each other through the internet. The cloud further includes management control module, consumption module, cloud environment module and memory module. The management control module is used as the background management and control module of cloud environment construction and cloud service and management.

The present invention further provides a sharing platform using an intelligent human centric lighting system as a human centric lighting, wherein the sharing platform includes: the intelligent human centric lighting system includes a cloud, a lighting field and a client terminal, and communicates with each other through the internet. The cloud further includes management control module, consumption module, cloud environment module and memory module. The management control module is used as the background management and control module of cloud environment construction and cloud service and management; a consumption module, which connected with the management control module to serve as a cloud service module subscribed and consumed by the client; a cloud environment module, which connected with the management control module and the consumption module, to provide a cloud management module of the intelligent human centric lighting system or an external or internal service of the client; a memory module, which connected to the management control module, the consumption module and the cloud environment module, and used as a storage module of the cloud background; the sharing platform provides the light environment of the intelligent human centric lighting system according to the following procedures. The procedures include: constructing a spectral recipe database, and the management control module stores the light scene data with specific color temperature into the memory module of the cloud to form the spectral recipe database, and takes the corresponding lighting parameters of the spectral recipe as the control parameters of the multispectral light-emitting device in the lighting field terminal to emit multi spectra, and each specific color temperature is the lighting parameter that makes a specific emotion have a synergistic and stimulating effect, and establishing a light environment platform, the management control module stores the lighting parameters of the spectral recipe to the cloud environment module in the cloud to form a sharing platform. Among them, the sharing platform is used to provide the client through the selection of the light scene, and the lighting parameters of the spectral recipe are used as the control parameters of the multispectral light-emitting device at the lighting field terminal to emit multispectral control parameters, so as to provide the light environment of the intelligent human centric lighting system to the client terminal to perform the lighting program.

The present invention further provides a sharing platform using an intelligent human centric lighting system as human centric lighting, which is characterized in that it includes the intelligent human centric lighting system. The intelligent human centric lighting system includes cloud, lighting field terminal and client terminal, and the cloud, lighting field terminal and client terminal communicate with each other through the internet. The cloud further includes: a management control module, a consumption module, a cloud environment module and a memory module. The management control module is used as the background management and control module of cloud environment construction and cloud service and management. The consumption module is connected with the management control module to serve as a cloud service module for client subscription and consumption. The cloud environment module is connected with the management control module and the consumption module to provide the intelligent human centric lighting system or the external or internal services of the client. The memory module, which is connected with the management control module, the consumption module and the cloud environment module as the storage module of the cloud background. The sharing platform provides the light environment of the intelligent human centric lighting system according to the following procedures. The procedures include constructing the spectral recipe database, which is that the management control module stores the light scene data with specific color temperature into the memory module to form the spectral recipe database, and takes the corresponding lighting parameters of the spectral recipe as the default value of lighting, each specific color temperature is the lighting parameter that makes a specific emotion have the synergistic stimulation effect. The lighting program is a lighting program for the client terminal according to the default value of the corresponding lighting parameters of the spectral recipe selected by the client terminal as the control parameter for the multi spectra emission of the multispectral light-emitting device at the lighting field terminal. Judge whether the lighting of the default value is effective after the client terminal completes the lighting program. If the client terminal thinks that the effect of specific emotional stimulation has been achieved, the lighting parameters of specific color temperature at this time will be stored. The management control module stores the lighting parameters of the spectral recipe into the cloud environment module to establish the light environment platform. The sharing platform is used to provide the user with the selection of spectral recipe, and the lighting parameters of spectral recipe are used as the control parameters of multispectral emission by the multispectral light-emitting device at the lighting field terminal, so as to provide the light environment of intelligent human centric lighting system and carry out the lighting program for the client terminal.

The present invention has provided the process of building various "spectral recipe" and the database of "spectral recipe" building services, as well as the database of hardware services and software services required for the construction of "spectral recipe", which have been established on the "sharing platform" of the optical environment. In particular, the "sharing platform" finally established is a "spectral recipe" that can provide effective spectral combination of multi-light scenes and spectral combination of multi emotional light scenes. After that, it can provide various commercial services and operations through this common "sharing platform".

DETAILED DESCRIPTION OF THE PREFERRED EMBODIMENT

Figure 1A:
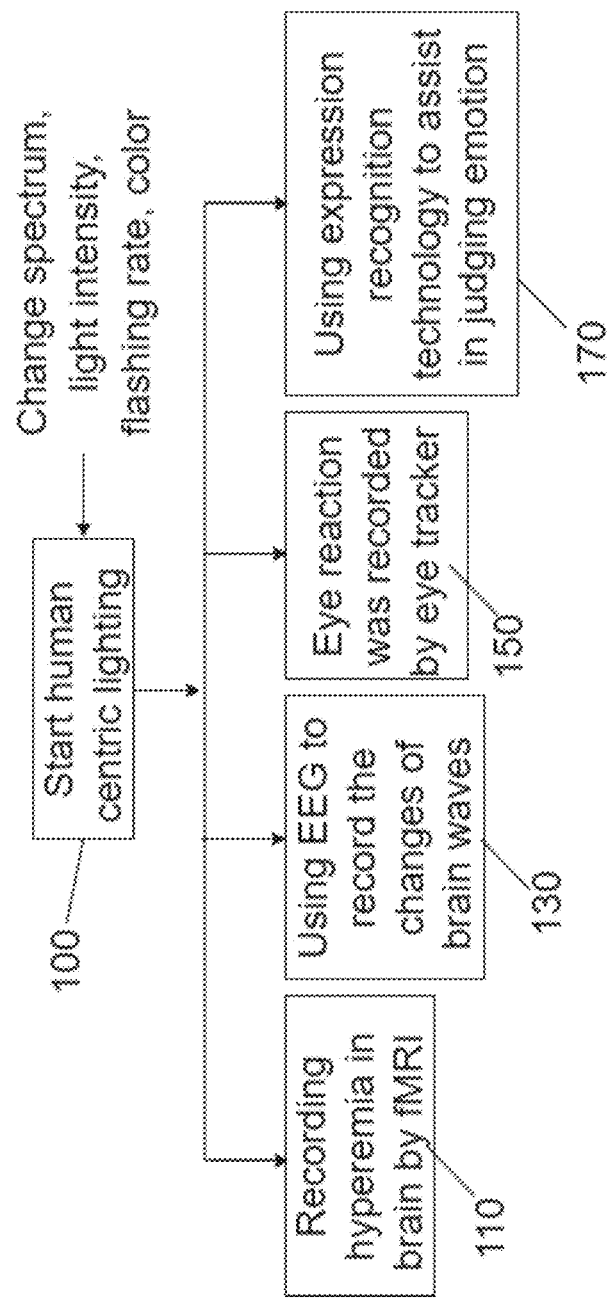
FIG. 1a is the original data collection structure of the human centric lighting to physiological and emotional according to the present invention.

In the specification after the present invention, the functional magnetic resonance imaging system is referred to as "fMRI system", the electroencephalograph is referred to as "EEG", and the blood oxygen-level dependent comparison is referred to as "BOLD". In addition, in the embodiment of the color temperature test of the present invention, the test is carried out in units of every 100k. However, in order to avoid too lengthy description, in the following description, the so-called specific emotion refers to excitement or excitement, happiness, amusement, etc., and the corresponding specific emotional response will be explained with 3,000K, 4,000K and 5,700K as color temperature test examples, Therefore, the present invention cannot be limited to the embodiments of the three color temperatures. At the same time, in order to make those in the technical field of the present invention fully understand the technical content, relevant embodiments and embodiments thereof are provided for explanation. In addition, when reading the embodiment provided by the present invention, please also refer to the schema and the following description, in which the shape and relative size of each component in the schema are only used to assist in understanding the content of the embodiment, not to limit the shape and relative size of each component.

The present invention uses fMRI system to understand the corresponding relationship between spectrum and emotion in the brain through physiological signal measurement method, and receipts a set of preliminary mechanism of using light to affect human physiological and psychological reactions, because the brain imaging of fMRI system can judge, which part of the human brain has hyperemia reaction when stimulated by light, it can also record BOLD reaction. This BOLD response to brain hyperemia is also known as the "rise of blood oxygen concentration dependent response". Therefore, according to the image recording data of brain hyperemia under various emotions of fMRI system and the response of "rise of blood oxygen-level dependent response", the present invention can accurately and objectively infer the physiological and emotional changes of the tester, and then take the physiological and emotional confirmed by fMRI system as the basis, further, EEG is used to record the changes of EEG to establish the correlation between them, in order to use the changes of EEG to replace the emotion judgment of fMRI system.

Therefore, the main purpose of the present invention is to enable the tester to record the BOLD response of the tester to the specific emotion after illuminating the tester during the test of specific emotion in the fMRI system, so as to screen out which specific "effective color temperature" can multiply the specific emotion, the color temperature of lighting is used as the "effective color temperature" corresponding to specific emotions. After that, the tester is illuminated with "effective color temperature", and the EEG is used to record the brainwave patterns under the stimulation of "effective color temperature", so that the specific brainwave patterns of the EEG is related to the specific BOLD response. After that, the user's emotional change can be assisted by the specific EEG mode of the EEG, in order to construct a set of intelligent human centric lighting system and its method that can be operated commercially, so as to solve the problem that expensive fMRI system must be used to execute intelligent human centric lighting system, which can reduce the operation cost and further meet the customized service demand.

First, please refer to FIG. 1a, which is the original data collection framework of physiological and emotional due to human centric lighting of the present invention. As shown in FIG. 1a, starting the intelligent human centric lighting system 100 is in an environment where various adjustable lighting modules have been configured (e.g., a test space), and provides light signal lighting parameters such as spectrum, light intensity, flicker rate and color temperature that can be changed. For different target emotions, the present invention uses the fMRI compatible image interaction platform 110 formed by the fMRI system to guide the emotion of voice and image, and at the same time, it is matched with a specific effective spectrum to stimulate for 40 seconds. Observe the changes in the area where the blood oxygen-level changes in the tester's brain to verify whether the "effective color temperature" can significantly induce the tester's emotional response, and the details are as follows.

Figure 1B:
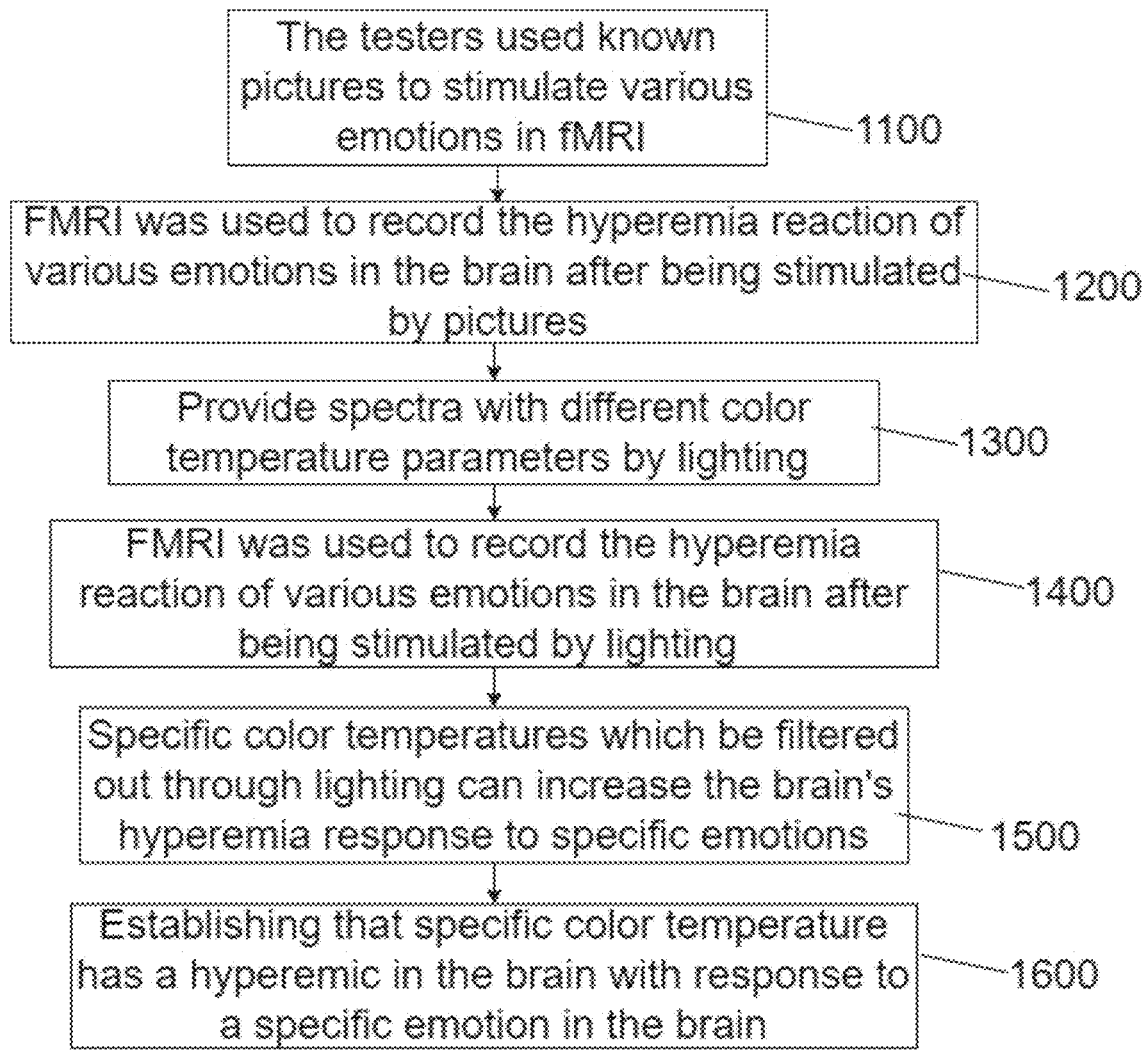
FIG. 1b is the original data collection of the human centric lighting to physiological and emotional according to the present invention.
Figure 1C:
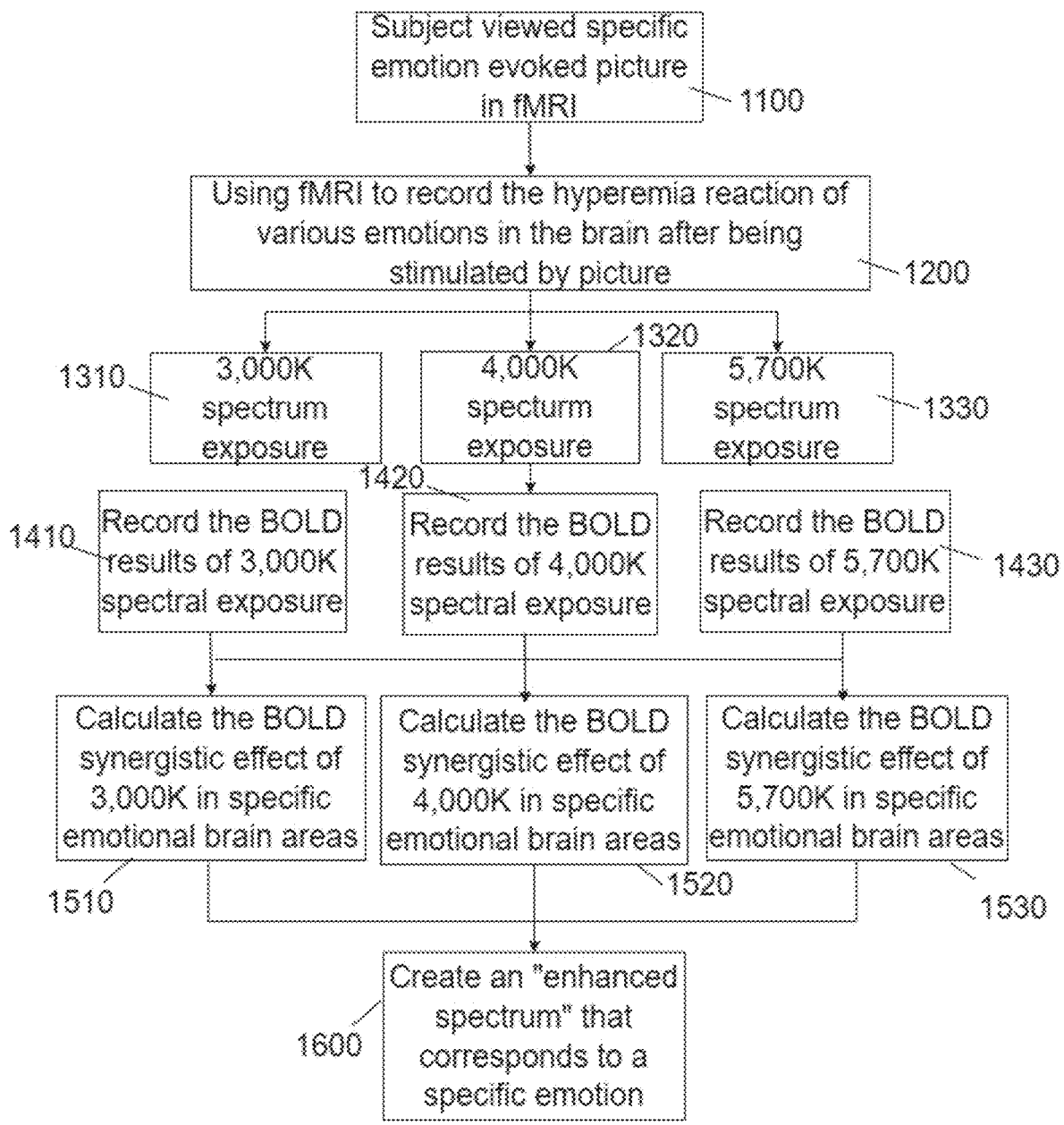
FIG. 1c is the judgment flow for the response of human centric lighting to specific physiological and emotional according to the present invention.

Next, please refer to FIG. 1B and FIG. 1c, wherein FIG. 1B is a flow chart of collecting original data of human centric lighting to physiological and emotional responses according to the present invention, and FIG. 1c is a judging flow of human centric lighting to specific physiological and emotional responses. As shown in step 1100 in FIG. 1B, each tester has been positioned on the compatible image interaction platform 110, and then each tester is guided to stimulate various emotions through known pictures. Afterwards, as shown in step 1200, the BOLD response in the brain of the tester's various emotions after being stimulated by the picture is recorded through the compatible image interaction platform 110. Next, as shown in step 1300, the tester is visually stimulated by irradiating light to provide spectrums with different color temperature parameters. For example, use LED lamps with electronic dimmers to provide spectrums with different color temperature parameters. In the embodiment of the present invention, nine groups of visual stimuli with different color temperatures, including 2,700K, 3,000K, 3,500K, 4,000K, 4,500K, 5,000K, 5,500K, 6,000K, and 6,500K, are provided. Among them, after completing 40 seconds of effective light irradiation and stimulation each time, you can choose to give testers one minute of invalid light source lighting (full spectrum non-flicker white light) to achieve the purpose of emotional relaxation. Further, it is also possible to choose to give the tester a 40 second counter effect light stimulation to observe whether the response in the area that responded to the original effective light stimulation decreased. In the embodiment of the present invention, after the compatible image interaction platform 110 has recorded the BOLD response in the brain of the tester's specific emotion after being stimulated by the picture, the tester is visually inspected by providing spectra with different color temperature parameters. The stimulus, as shown in step 1310 in FIG. 1c, is used to provide a spectrum with a color temperature of 3,000K, then, as shown in step 1320, to provide a spectrum with a color temperature of 4,000K, and finally, as shown in step 1330, to provide a color temperature for the 5,700K spectrum, the test subjects were visually stimulated.

Next, as shown in step 1400, the BOLD response of the test subject's brain after being stimulated by light is recorded through the compatible image interaction platform 110. In the embodiment of the present invention, after the tester is stimulated by lighting with different color temperature parameters, the compatible image interaction platform 110 records the BOLD response results with emotional response areas in the corresponding limbic system of the tester in sequence. Among them, the location of limbic system triggered by different emotions is different, and the above limbic system with emotional response in brain area is shown in Table 1 below.

TABLE 1

| Limbic system | Function |
| --- | --- |
| ACC | Emotion |
| Cuneus | Vision, Control bipolar disorder |
| Cerebellum | Balance, Coordination, Antidepressant & Anxiety |
| Insula Lobe | Affection, addiction |
| Lingual Gyrus | Logic, Vision ` Antidepressant & Anxiety |
| Rolandic Operculum | Emotion Management, Gustatory Sense |
| Superior Frontal Gyrus | Working Memory, Self-consciousness, laugh |
| Middle Temporal Gyrus | Emotion Recognition, Creativity |
| MCC | Emotion |
| Pallidum | Affection, Motion, Cognition, Reward System |
| Temporal Pole | Affection, Language, Auditory |

The compatible image interaction platform 110 records the response result of BOLD in a specific area of the brain, and the response result is judged by calculating the area of these emotional response parts when the brain area has more limbic system with BOLD emotional response, for example, when there is a BOLD emotional response the larger the area of emotional response, the stronger the response to a specific physiological and emotional. In the embodiment of the present invention, as shown in step 1410 in FIG. 1c, it is used to record the reaction result of BOLD with a color temperature of 3,000K after spectral irradiation, and then, as shown in step 1420, it is used to record the color temperature of 4,000K. Finally, as shown in step 1430, the reaction result of BOLD after spectral irradiation is used to record the reaction result of BOLD after spectral irradiation with a color temperature of 5,700K. Among them, after the tester passes through the lighting procedure after the excitement is induced, the compatible image interaction platform 110 records the response results of BOLD in a specific area of the brain as shown in Table 2.

TABLE 2

| Excitement Index | | | |
|---|---|---|---|
| Limbic system | 3,000K | 4,000K | 5,700K |
| ACC | 0 | 0 | −30 |
| Cerebellum | 577 | 0 | −75 |
| Middle Temporal Gyrus | 0 | 99 | 0 |
| Superior Frontal Gyrus | 0 | 127 | 0 |
| Total T Score | 577 | 226 | −105 |

Among them, after the tester passes through the lighting procedure induced by happiness, the compatible image interaction platform 110 records the response results of BOLD in a specific area of the brain as shown in Table 3.

TABLE 3

| Happiness Index | | | |
|---|---|---|---|
| Limbic system | 3,000K | 4,000K | 5,700K |
| ACC | 0 | 0 | −162 |
| Cerebellum | 163 | 252 | 0 |
| Pallidum | 80 | 0 | 0 |
| Insula Lobe | 85 | 307 | 0 |
| Lingual Gyrus | 0 | 58 | 403 |
| Temporal Pole | 0 | 57 | 0 |
| Total T Score | 328 | 674 | 241 |

Among them, after the tester passes through the lighting procedure after the emotion-induced amusement, the compatible image interaction platform 110 records the response results of BOLD in a specific area of the brain as shown in Table 4.

TABLE 4

| Amusement Index | | | |
|---|---|---|---|
| Limbic system of brain | 3,000K | 4,000K | 5,700K |
| Lingual Gyrus | 0 | 279 | 327 |
| Cerebellum | 539 | 215 | 226 |
| Middle Temporal Gyrus | 0 | 0 | 90 |
| MCC | −83 | 32 | 0 |
| Total T Score | 456 | 526 | 643 |

Afterwards, as shown in step 1500, the results of the BOLD reaction that a specific color temperature can increase a specific emotion are screened by lighting, and the specific color temperature is called an "effective color temperature". In this embodiment, the BOLD response result of the emotional response area in the limbic system of the tester's corresponding brain is recorded, so as to summarize the stimulation effect of color temperature on the brain, as shown in Tables 1 to 3 shown for the BOLD brain region-dependent response results that screened out the specific color temperature that can increase a specific emotion, we calculated those specific color temperature that can make the response effect of a specific emotion reach the maximum response value (that is, the maximum response area value with BOLD).

As shown in step 1510, when the tester has recorded the excitation emotion on the compatible image interaction platform 110 and finishes the lighting program again, the maximum response value is calculated. For example, according to the records in Table 2, the total score of 3,000K (577) is subtracted from the total score of 4,000K (226) to obtain 351. Then, after subtracting the total score (−105) of 5,700k from the total score (577) of 3,000K, 682 is obtained. The total score of response value under 3,000K lighting after excitation is 1033.

Next, as shown in step 1520 in FIG. 1c, when the tester has recorded the excitation emotion on the compatible image interaction platform 110 and completed the lighting program again, it starts to calculate the maximum response value. For example, according to the records in Table 2, subtract the total score (226) of 4,000K from the total score (577) of 3,000K to obtain −351. Then, after subtracting the total score (−105) of 5700k from the total score (266) of 4,000K, 371 is obtained.

Then, as shown in step 1530 in FIG. 1c, after the tester has recorded the excitation emotion induction on the compatible image interaction platform 110 and completed the lighting program, it starts to calculate the maximum response value. For example, according to the records in Table 2, after subtracting the total score (−105) of 5,700K from the total score (577) of 3,000K, it obtains −682. Then, the total score (−105) of 5,700K is subtracted from the total score (−105) of 4,000K to obtain 371.

According to the above calculation, after the excitation emotion is induced, the excitation emotion can reach the maximum response value at 3,000K lighting. That is, 3,000K lighting can make excitement get a more obvious additive effect (that is, compared with the total calculated score of 4,000K and 5,700K lighting, the total calculated score of 3,000K lighting is 1033, the highest). Therefore, 3,000K illuminance is used as the "effective color temperature" of excitement. For other emotions, such as "effective color temperature" of happiness and amusement, different "effective color temperatures" can be obtained from the above calculation results in steps 1510 to 1530, as shown in Table 5 below.

TABLE 5

| Emotion | Effective Color Temperature |
|---|---|
| Excitement | 3,000K |
| Happiness | 4,000K |
| Amusement | 5,700K |

Next, according to the statistical results in Table 5, the effective color temperature can be regarded as the result of a specific physiological and emotional-dependent response, and this effective color temperature can be regarded as the "enhanced spectrum" of the "blood oxygen-level dependence" of fMRI on a certain emotion. For example, an effective color temperature of 3,000K can represent the "enhanced spectrum" of the fMRI system in "excited" emotions. For example, an effective color temperature of 4,000K can represent the "enhanced spectrum" of the fMRI system in "happy" emotions. For example, the effective color temperature of 5,700K can represent the "enhanced spectrum" of the fMRI system in "amusement" emotions.

Finally, as shown in step 1600, an "enhanced spectrum" database corresponding to the effect of a particular emotion can be established in the fMRI system. The tester is stimulated by the above-mentioned human centric lighting parameters, and the BOLD response of the tester's brain when the tester's brain is stimulated by light is observed and recorded through the fMRI system. The additive and multiplicative response of "blood oxygen-level dependence increase" makes a specific effective color temperature can be regarded as the "enhanced spectrum" of the "blood oxygen-level dependence" of fMRI for a specific emotion. Obviously, the present invention objectively deduces the tester's "enhanced spectrum" under a specific physiological and emotional response based on the statistical result of the BOLD reaching a specific emotional response at a specific "effective color temperature" in Table 5, and This "enhanced spectrum" is used as the evidence of the most synergistic physiological and emotional response to a specific emotion. (Including: excitement, happiness, amusement, anger, disgust, fear, sadness, calm, or neutrality)

It should be emphasized that, in the entire implementation process of FIG. 1B and FIG. 1c, the statistical results in Table 5 are obtained after 100 testers are respectively subjected to a complete test of multiple specific emotions. For example, in terms of excitement, providing an effective color temperature of 3,000K as the "enhanced spectrum" under the excited physiological and emotional response can make the tester's excited emotions produce the most synergistic physiological-emotional response. For example, in terms of happy emotions, providing an effective color temperature of 4,000K as the "enhanced spectrum" under the happy physiological and emotional response can make the tester's happy emotions produce physiological and emotional responses with the strongest synergistic effect. Another example, in terms of amusement emotions, providing an effective color temperature of 5,700K as an "enhanced spectrum" under the amusement physiological and emotional response can make the tester's amusement emotions produce a physiological and emotional response with the strongest synergistic effect.

In addition, it should also be emphasized that the above-mentioned three color temperatures are only representative of the embodiments of the present invention, and not only the lighting of the three color temperatures is used as the "enhanced spectrum" under the three physiological and emotional responses. In fact, the whole process of FIG. 1b and FIG. 1c can be carried out for different emotions (including excitement, happiness, amusement, anger, disgust, fear, sadness, calm or neutral) after 2,000K color temperature is increased by 100K as an interval. Therefore, Table 5 of the present invention is only the result of the disclosure part, not to limit the present invention. The invention is only limited to these three embodiments.

Next, the present invention is to establish an artificial intelligence model of "the correlation between brainwaves and brain images of general physiological and emotional", so that in future commercial promotion, the results of other sensing devices can be directly used to infer physiological and emotional without using fMRI system. Among them, the sensing device matched with the present invention includes electroencephalograph (EEG). In the following embodiments, the electroencephalograph 130 is used to establish the human centric physiological and emotional response to light, and the eye tracker 150 or the expression recognition technology auxiliary program 170 can be used to replace the fMRI system's response to physiological and emotional. However, the eye tracker 150 or the expression recognition technology auxiliary program 170 will not be disclosed in the present invention, but will be announced first.

Figure 2A:
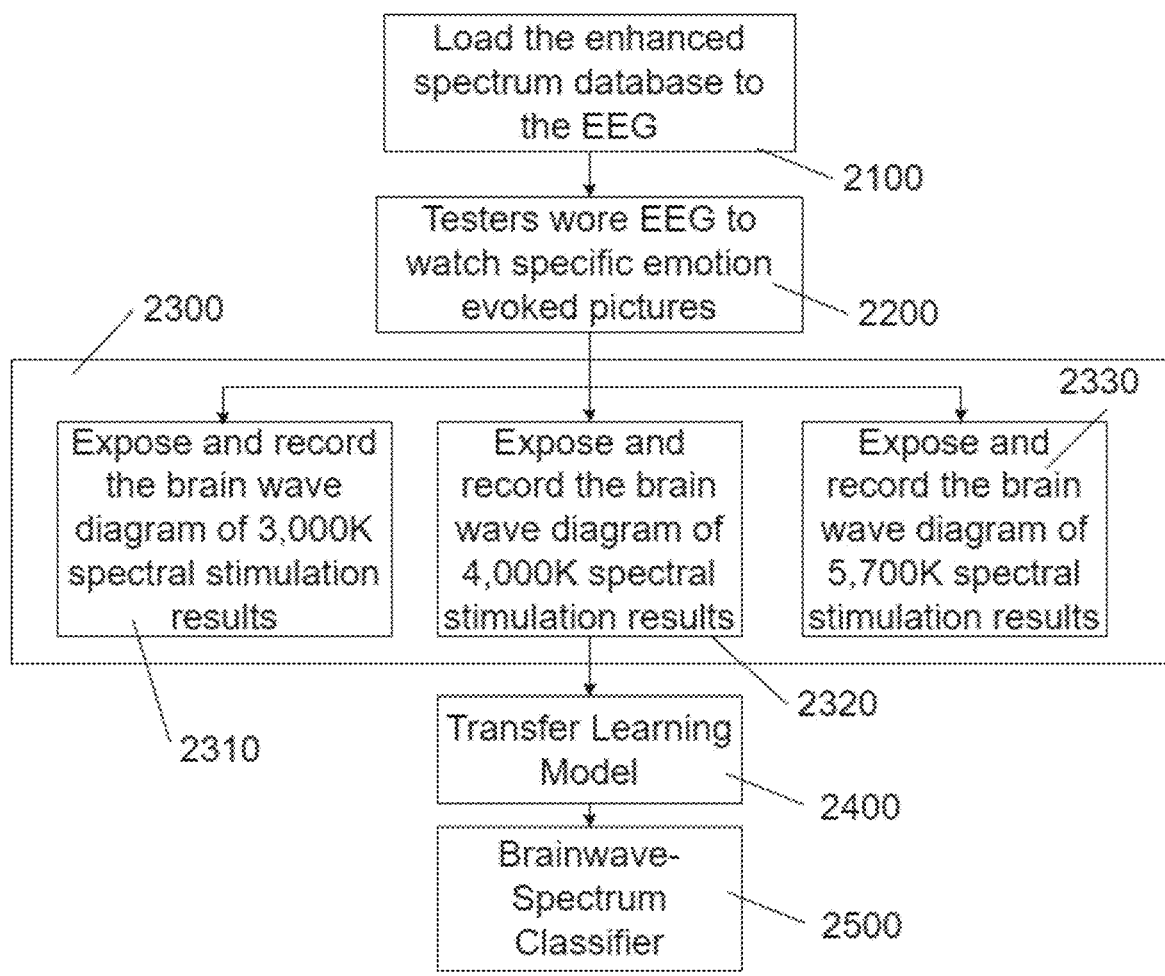
FIG. 2a is a method for establishing the response of EEG of human centric lighting to physiological and emotional.

Please refer to FIG. 2a, which is a method for establishing a human centric lighting electroencephalogram response to physiological and emotional according to the present invention. As shown in FIG. 2a, the present invention is a method for establishing the human centric lighting response to physiological and emotional through the electroencephalograph 130, including, first, as shown in step 2100, the "enhanced spectrum" database information in Table 5 is also stored in the memory of the electroencephalograph 130. Next, as shown in step 2200, let the testers wear the EEG, and guide each tester to stimulate various emotions through the elements of known pictures or videos. Afterwards, as shown in step 2300, the intelligent human centric lighting system 100 is activated, and light signal parameters such as spectrum, light intensity, flicker rate, and color temperature that can be changed are provided to stimulate the tester with light. Next, the electroencephalogram file after being illuminated with different color temperatures under a specific emotion is recorded by the electroencephalograph 130. For example, in this embodiment, each tester is first stimulated with excitement, and then, in steps 2310 to 2330, different color temperatures of 3,000K, 4,000K and 5,700K are provided to stimulate the tester respectively, and the tester is recorded in when stimulated by excitement, the electroencephalogram file of the specific emotion after the tester is illuminated with different color temperatures is stored in the device in the memory of the electroencephalograph 130. In the embodiment of the present invention, the electroencephalogram files after 100 testers have completed specific emotional stimulation and lighting have been recorded respectively, therefore, a larger memory is required.

Next, as shown in step 2400, the electroencephalogram files of specific emotions (e.g., excitement, happiness, amusement) stored in the memory of the electroencephalograph 130 is learned through the learning method of artificial intelligence. Since the electroencephalograph 130 can only store the waveform of the electroencephalogram, the electroencephalogram currently stored in the memory of the electroencephalograph 130 is the electroencephalogram file after a known specific triggering emotional stimulus and lighting of different color temperatures. It should be noted that, in the actual test, different testers have different electroencephalogram files for the same emotional stimulus and lighting with the same color temperature. Therefore, during the learning process of step 2400, the present invention needs to classify the electroencephalogram files of specific emotions through the information of the "enhanced spectrum" database, group the electroencephalogram files with a color temperature of 3,000K, for example, For the electroencephalogram files of happy emotions, only group the electroencephalogram files of different testers with a color temperature of 4,000K. Another example, for the electroencephalogram file of happy mood, only the electroencephalogram files of different testers at 4,000K color temperature are grouped, for example, for the electroencephalogram file of happy mood, only the electroencephalogram files of different testers at 5,700k color temperature are grouped. Then, the EEG is trained through machine learning in artificial intelligence. In the embodiment of the present invention, in particular, a transfer learning model is selected for learning and training.

In the process of learning and training using the transfer learning model in step 2400, the group of electroencephalogram files for specific emotions is learned and trained by counting, calculating and comparing the similarity. For example, when learning and training the group of electroencephalogram files with 3,000K color temperature, it is based on statistics, calculation and comparison of the ranking of the highest similarity and the lowest similarity among the electroencephalogram files with 3,000K color temperature. For example, the ranking with the highest similarity can be regarded as the electroencephalogram file with the strongest emotion, the ranking with the lowest similarity can be regarded as the electroencephalogram file with the weakest emotion, and the electroencephalogram file with the strongest emotion can be regarded as the electroencephalogram file. As the "target value", the electroencephalogram file with the weakest emotion ranking is used as the "starting value". For the convenience of explanation, the most similar at least one electroencephalogram file is taken as the "target value", and the least similar at least one electroencephalogram file is taken as the "start value", and different scores are given, for example, "target value" is given 90 points for similarity, and 30 points for "initial value". Similarly, complete the electroencephalogram files of the series of happy emotions in the 4,000K color temperature category, and the electroencephalogram files of the series of the surprised emotions in the 5,700K color temperature category. Among them, the "start value" and "target value" can be formed into a score interval of similarity.

Afterwards, as shown in step 2500, an electroencephalogram classification and grading database in artificial intelligence (it may be referred to as an artificial intelligence electroencephalogram file database) is established. After the step 2400 is passed, the classification results of the "target value" score and the "start value" score are given to the electroencephalogram file groups of various specific color temperatures to form a database, which is stored in the memory of the electroencephalograph 130. The purpose of establishing the electroencephalogram classification and grading database in step 2500 of the present invention is to obtain the electroencephalogram file of the unknown tester after receiving a specific emotional stimulus and giving lighting of a specific color temperature to an unknown tester. After the similarity score interval between the electroencephalogram file of the unknown tester and the electroencephalogram file in the database is compared, it can be used to judge or infer the current state of the unknown tester's hyperemia reaction in the brain. The detailed process is shown in FIG. 2b shown.

Figure 2B:
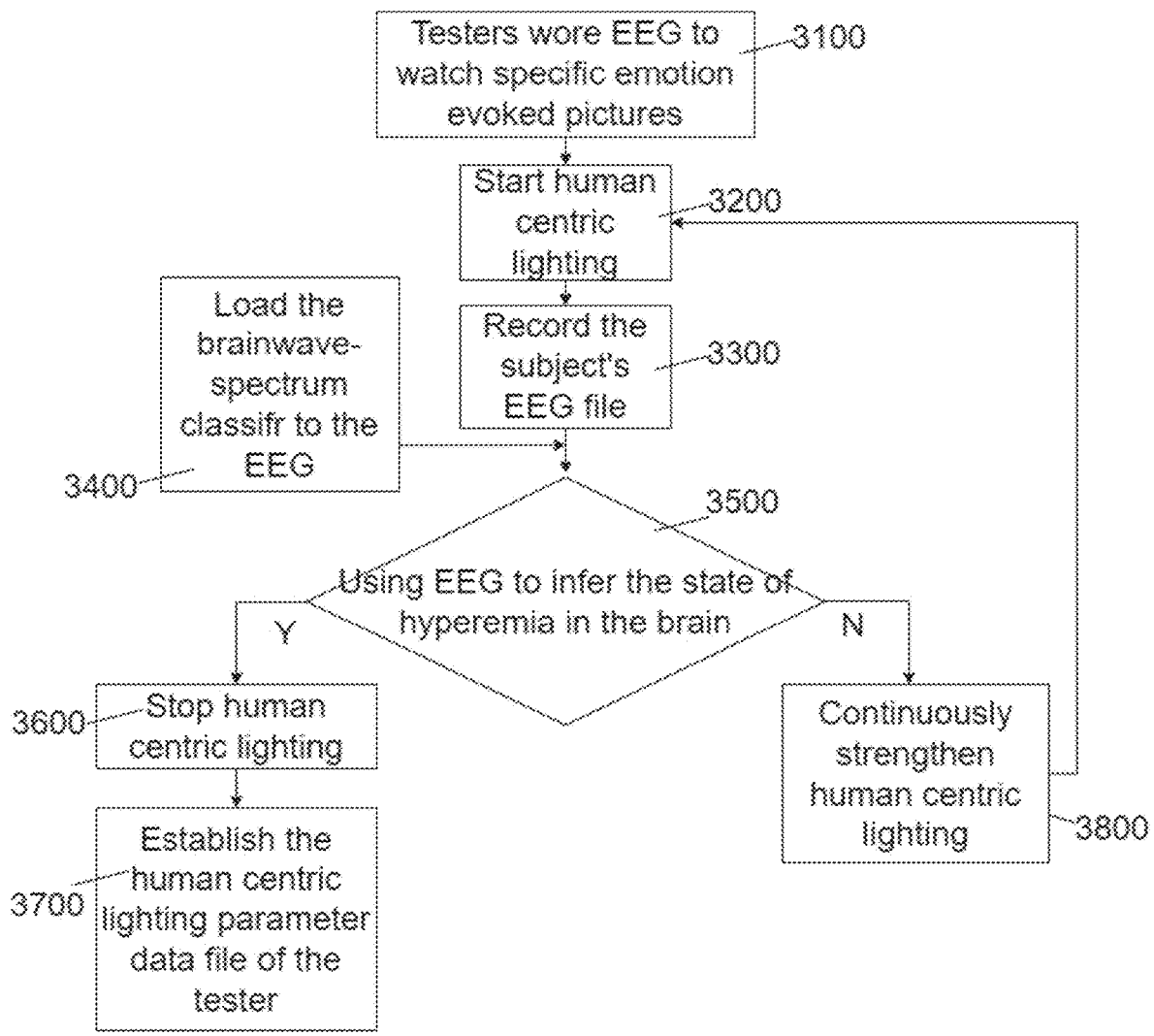
FIG. 2b is the lighting database that the present invention constructs the user to carry out effective human centric lighting.
Figure 3:
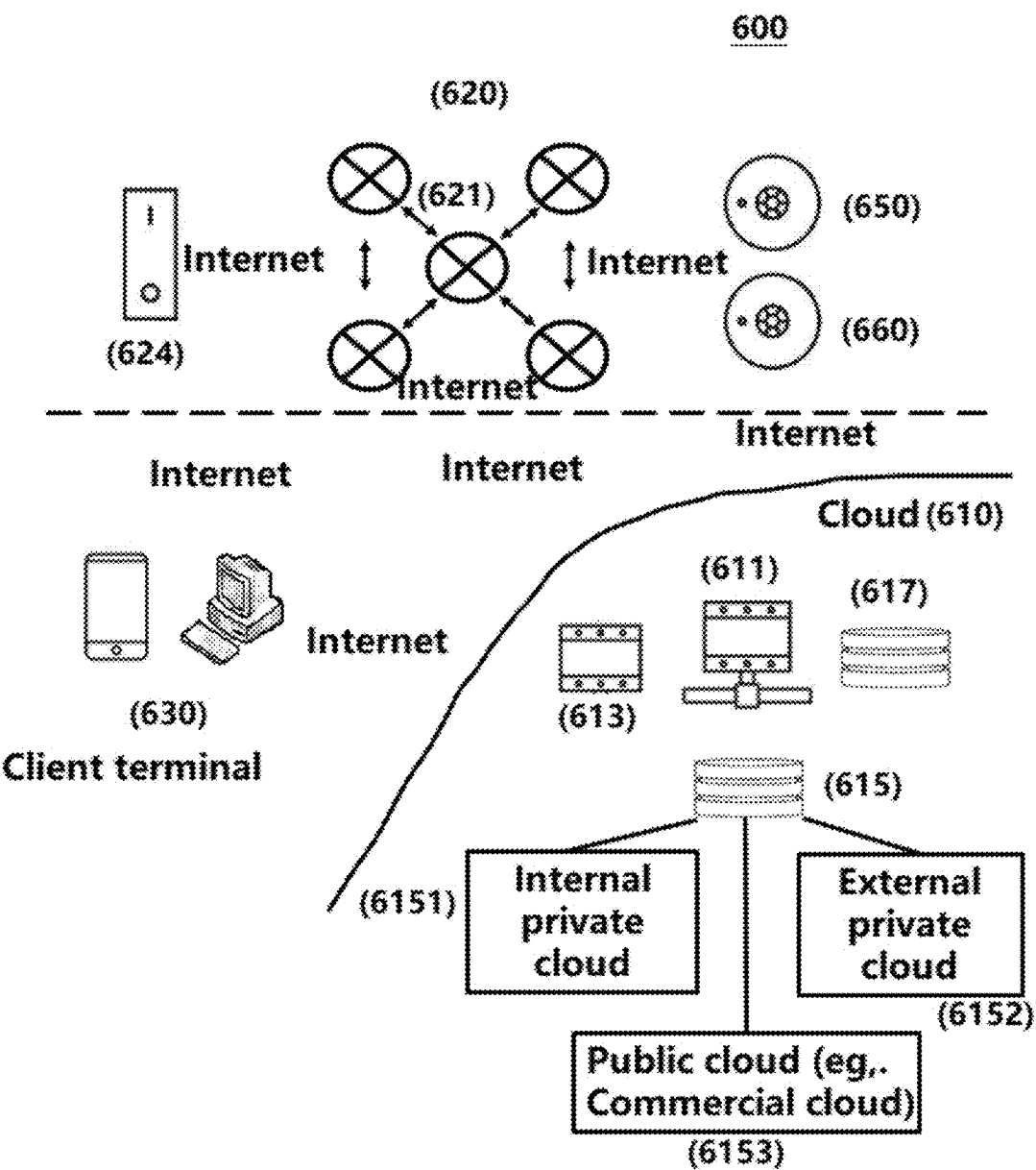
FIG. 3 is the system frame diagram of the intelligent human centric lighting system of the present invention.

Next, please refer to FIG. 2b, which is a lighting database for constructing a user's effective human centric lighting according to the present invention. First, as shown in step 3100, the tester is put on the electroencephalograph 130, and the tester is allowed to watch a picture evoked by a specific emotion. Afterwards, as shown in step 3200, the intelligent human centric lighting system 100 is activated by management control module 611 (as shown in FIG. 3) in an environment (e.g., a test space) that has been configured with various adjustable multispectral lighting modules. To provide light parameters such as spectrum, light intensity, flashing rate, color temperature and other light signal light parameters that can be changed. Next, as shown in step 3300, obtain the electroencephalogram file of the tester after the induced emotion and lighting, and store it in the memory module 617 of the cloud 610 (as shown in FIG. 3). Next, as shown in step 3400, import the artificial intelligence electroencephalogram file database into the management control module 611. Wherein, the management control module 611 will set a score of whether the similarity is sufficient. For example, when the similarity score is set to be more than 75 points, it means that the tester's brain hyperemia reaction is sufficient. Next, as shown in step 3500, in the management control module 611, the similarity between the tester's electroencephalogram file and the artificial intelligence electroencephalogram file is compared. For example, when the similarity score of the tester's electroencephalogram files after comparison is 90 points, the management control module 611 immediately judges that the tester's brain hyperemia reaction is very sufficient, so it will go to step 3600 to terminate the person with a specific emotion Due to lighting test. Next, go to step 3700, record the human centric lighting parameters in the tester's brain when the hyperemia response has reached the stimulus, into a database and store in the memory module 617.

Next, in the procedure of step 3500 in FIG. 2b, if the similarity score after the comparison between the tester's electroencephalogram file and the artificial intelligence electroencephalogram file is 35 points, the management control module 611 will determine the tester's brain If the hyperemia reaction is insufficient, step 3800 will be performed, and the management control module 611 will continue to strengthen the human centric lighting test, including: according to the similarity score, the management control module 611 can control it to provide an appropriate increase in the lighting time or increase light intensity. Then, the electroencephalogram file after increasing the illumination time or intensity is obtained again through step 3300. After step 3400, the human centric lighting test is not stopped until the similarity score reaches the set similarity score of more than 75 points. Wherein, when the management control module 611 determines that the hyperemia reaction in the tester's brain has reached the stimulation, in step 3700, a data file of the human centric lighting parameters of the tester is created. Finally, the management control module 611 will form a "human centric lighting parameter database" of the human centric lighting parameters of each tester and store it in the memory module 617. Obviously, when there are more testers, the artificial intelligence electroencephalogram file database of the present invention will learn more electroencephalogram files, so that the similarity score of the present invention is more and more accurate.

After the artificial intelligence model of the "human centric lighting parameter database" is established, after the intelligent human centric lighting system 100 is activated, the present invention can deduce the result only by observing the electroencephalogram file of the electroencephalograph 130, that is, it can be deduced The physiological and emotional changes in the brain images of the new test subjects can be inferred based on the artificial intelligence model of the "Human Centric Lighting Parameter Database" without using a high-value fMRI system. So that the intelligent human centric lighting system 100 can be promoted and used commercially. In addition, in order to enable the "human centric lighting parameter database" to be used commercially, the "human centric lighting parameter database" may be further stored in the internal private cloud 6151 in the cloud 610.

Next, please refer to FIG. 3, which is a system architecture diagram of the intelligent human centric lighting system 100 of the present invention. As shown in FIG. 3, the overall architecture of the intelligent human centric lighting system 100 of the present invention can be divided into three blocks, including: a cloud 610, a lighting field terminal 620 and a client terminal 630. The internet is used as a connection channel, so the three blocks can be distributed in different areas, and of course they can be configured together. The cloud 610 further includes: a management control module 611, which is used for cloud computing, cloud environment construction, cloud management or use of cloud computing resources, etc., and also allows users to access, construct or modify the content in each module through the management control module 611. The consumption module 613 is connected with the management control module 611 and is used as a cloud service subscribed and consumed by the user. Therefore, the consumption module 613 can access various modules in the cloud 610. The cloud environment module 615, connected with the management control module 611 and the consumption module 613, divides the cloud background environment into an internal private cloud 6151, an external private cloud 6153, and a public cloud 6155 (for example, a commercial cloud), etc., and can provide system providers or an interface to a user's external or internal service. The memory module 617 is connected to the management control module 611 and is used as a storage area of the cloud background. The technical contents required to be executed by each module in the present invention will be described in detail in the subsequent different embodiments. The lighting field terminal 620 can communicate with the cloud 610 or the client terminal 630 through the internet. The lighting field terminal 620 is provided with a LED lamps group 621 composed of a plurality of light-emitting devices. And the client terminal 630 can communicate with the cloud 610 or the lighting field terminal 620 through the internet. Among them, the client terminal 630 of the present invention includes general users and editors who use the intelligent human centric lighting system 100 of the present invention for various commercial operations, all of which belong to the client terminal 630 of the present invention, and the representative device of the client terminal 630 or the device can be a fixed device with computing function or a portable intelligent communication device. In the following description, the user, creator, editor or portable communication device can all represent the client terminal 630. In addition, in the present invention, the above-mentioned internet may be an Artificial Intelligence of Things (AIoT).

Figure 4:
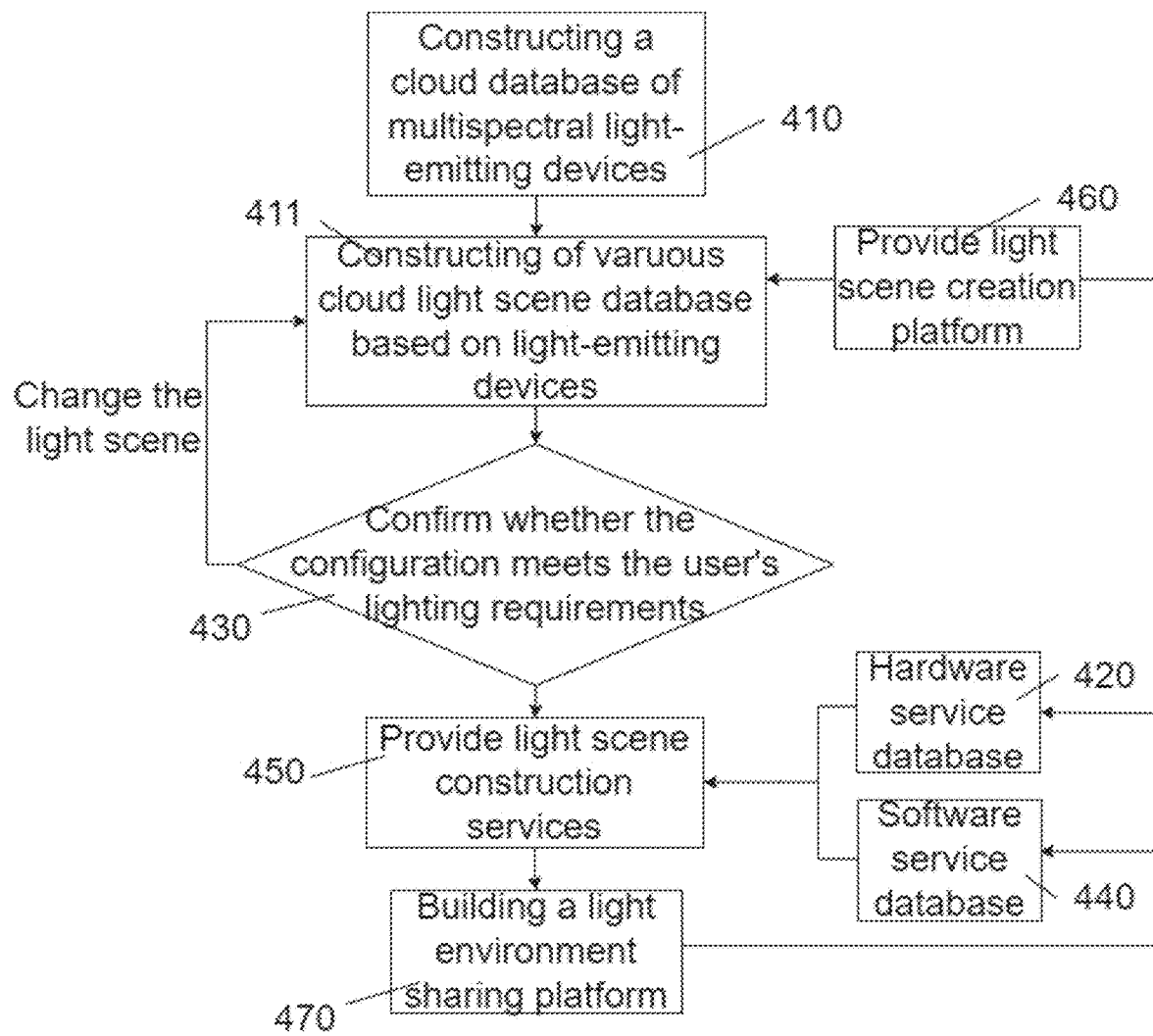
FIG. 4 is a method for constructing a human centric light environment platform of the present invention.

Please refer to FIG. 4, which is a method for constructing light environment platform 400 according to the present invention. In the process of FIG. 4, the process is performed in the system of the intelligent human centric lighting system 100 in FIG. 3, wherein the intelligent human centric lighting system 100 has a plurality of LED lamps group 621 providing different spectrums. In particular, the present invention should illustrate that the LED lamps group can selectively modulate the voltage or current of the individual LED lighting to combine a multispectral combination with a specific color temperature, so as to provide a multispectral combination for lighting. Of course, the present invention can also choose to use a plurality of LED lamps with a specific luminous spectrum, by providing a fixed voltage or current to make each LED lamps that is energized emit its specific spectrum to combine a multispectral combination with a specific color temperature come to light. In addition, it should be emphasized that the LED lamps group 621 with different spectrums in the present invention need to emit different spectrums through a plurality of LED lamps group 621 according to the actual lighting process. Therefore, the LED lamps group 621 with different spectrums can be composed of different. The spectrum of light-emitting devices can also be composed of multiple identical light-emitting devices, and the spectrum emitted by the light-emitting devices can be modulated into different spectrums by controlling the power provided by the device. Therefore, the present invention does not limit the embodiments of the above LED lamps group 621 with different spectrums, and of course also includes light-emitting devices with different spectrums formed by other means.

First, as shown in step 410, a multispectral light emitting device cloud database is constructed. The "human centric lighting parameter database" stored in the memory module 617 or stored in the internal private cloud 6151 is loaded into the management control module 611 by the management control module 611 in the cloud 610. Among them, the "human centric lighting parameter database" stored in the cloud 610 already knows that various color temperatures can make people (or users) get corresponding emotional stimulation. For example, a specific color temperature can make a specific emotion have a stimulating effect of a multiplicative response.

Next, as shown in step 411, a cloud database of light scenes of the multispectral lighting device is to be constructed. Since each color temperature can be combined by different multiple spectrums, that is to say, the same color temperature can be combined by different multiple spectrums. For example, when we want to build a spectrum that can provide 4,000K color temperature, we can choose the multispectral combination of Maldives at 4,000K color temperature, or we can choose the multispectral combination of 4,000K color temperature in Bali, Indonesia, or further choose Monaco Beach at 4,000K multispectral combination of color temperature. Obviously, these multispectral combinations with a color temperature of 4,000K have different multispectral combinations according to their geographical location (including latitude and longitude), time/brightness/flashing rate and other factors. Therefore, in step 411, according to the relationship between the color temperature and the corresponding emotions in the "human centric lighting parameter database", the cloud 610 can collect different multispectral combinations of specific color temperatures in different geographical locations on the earth, for example, collecting on the earth different multispectral combinations at 4,000K color temperature in different geographic locations (e.g., 4,000K color temperature at different latitude and longitude), or collect different multispectral combinations at 4,000K color temperature at different times on earth (e.g., 4,000K color temperature at 9:00 am). Afterwards, the collected different multispectral combinations of different geographic locations on the earth at specific color temperatures are also stored in the memory module 617. Through the control of the management control module 611 in the intelligent human centric lighting system 100, the parameters of various multispectral combinations with specific color temperature (i.e., time at different geographical locations or locations) can be adjusted by controlling a plurality of LED lamps group 621 with different spectra, which are stored in the memory module 617. The intelligent human centric lighting system 100 of the present invention can construct a "cloud database of multispectral light-emitting devices" with multispectral combinations of various color temperatures formed in different geographical locations. Obviously, the "multispectral light emitting device cloud database" constructed in step 411 is the result of adjustment by multiple LED lamps group 621 with different spectra. In addition, it should be emphasized that after mastering the stimulation effect that different specific color temperatures can make specific emotions have additive reaction, when forming the multispectral combination of various color temperatures, in addition to the multispectral combination according to different geographical locations on the earth, the present invention can also consider different longitude and latitude/time/brightness/flicker rate and other factors through artificial intelligence, The invention does not limit the synthesis or combination of multispectral combinations different from the actual geographical location. Obviously, in step 411, the present invention has constructed a light scene database with multispectral light emitting device cloud database. Therefore, according to the constructed database of different light scenes, the intelligent human centric lighting system 100 can provide multispectral lighting services under different color temperatures through the multispectral lighting device. At this time, the "multispectral light emitting device cloud database" constructed in step 411 can be stored in the memory module 617 or in the internal private cloud 6151 or in the public cloud 6155 (e.g., commercial cloud).

As shown in step 430, it is determined whether the lighting of the multispectral combination is effective. Since different users may have different effects on emotional stimulation or influence through the spectrum of human centric lighting, it is necessary to adjust the lighting spectrum of the multispectral combination. Next, when the client terminal 630 enters the intelligent human centric lighting system 100 of the present invention, he can go through the management control module 611 to the memory module 617 or the "multispectral light emitting device cloud database" in the internal private cloud 6151 or the public cloud 6155, select the emotion you want to achieve. After that, the management control module 611 can go to the memory module 617 or the "multispectral light emitting device cloud database" in the internal private cloud 6151 or the public cloud 6155, select a default multispectral combination, and control multiple different spectrums The LED lamps group 621 is used to adjust the multispectral combination of the desired mood, and let the adjusted multispectral combination perform a lighting program for the user. For example, when the user wants to adjust the mood to happiness or amusement, according to the "human centric lighting parameter database", the user can choose to use the color temperature of 4,000K to illuminate. At this time, the user can go to the default multispectral combination provided by the "multispectral light emitting device cloud database", or the user can choose a multispectral combination that can provide the color temperature of 4,000K, of course, the user can also choose a specific multispectral combination used by the most people for irradiation. At this time, when the user uses the multi spectral combination provided by the intelligent human centric lighting system 100 in the "multispectral light emitting device cloud database", the present invention is called the default multispectral combination.

Next, as shown in step 430, when the user selects a multispectral combination preset as happiness or amusement (for example, the system defaults to the multispectral combination of Maldives at 4,000K color temperature), and carries out the lighting program through the multispectral combination adjusted by a plurality of LED lamps group 621 with different spectra, for example, after 15 minutes of lighting program, The user can judge or evaluate whether the multispectral combination of irradiation has effectively achieved happiness or pleasant emotion. Among them, the way for users to judge or evaluate whether they have effectively achieved happiness or amusement emotions can be determined according to their own feelings.

Continuing as shown in step 430, when the user intuitively feels that he or she has effectively achieved a happy or amusement mood, the user experience can be recorded and stored in the external private cloud 6153 or the public cloud 6155, for example, after the record of use experience is stored in the external private cloud 6153, it can be used as the user's own use experience file. For example, of course, the use experience can also be recorded and stored in the public cloud 6155 to provide reference for other users. If the user does not feel happy or amusement after 15 minutes of lighting, the user can adjust the multispectral combined spectral recipe through the management control module 611, for example, adjust the lighting time to 30 minutes, or replace for a multispectral combination light scene, for example, go back to step 411 to reselect another multispectral combination light scene, and replace the multispectral combination light scene from the default Maldives to Bali, Indonesia. After that, in step 430, the multispectral lighting procedure is performed again for 15 minutes, and after the lighting procedure is completed, it is judged or evaluated again whether the lighting of Bali's multispectral combination has effectively achieved a happy or amusement. Until the user feels that after the multispectral lighting of the current light scene, the happy or amusement mood has been effectively achieved, the effective light scene use experience can be recorded and stored to form a "spectral recipe", and finally, and store this "spectral recipe" in the external private cloud 6153 or the public cloud 6155 to form a shared platform. Obviously, there are multiple "spectral recipe" stored in the shared platform. The contents stored in the shared platform include: the lighting control parameters of the light scene in which the user achieves the specific emotional effect and the multispectral combination of the LED lamps group 621 with multiple different spectra generating the specific emotional light scene (hereinafter referred to as the lighting parameters).

Finally, as shown in step 470, a light environment platform is constructed. After the user records and stores the effective use experience in the external private cloud 6153 or public cloud 6155, in addition to being the user's own use experience file, the intelligent human centric lighting system 100 can record and store the effective experience data of many users in the internal private cloud 6151 or public cloud 6155 after massive data analysis in step 470, The information stored in the public cloud 6155 forms a "sharing platform" of the optical environment. For example, the intelligent human centric lighting system 100 can analyze the massive data of many users' experience data, and then can obtain the ranking of the "spectral recipe" of different light scenes with specific color temperature selected by the user. This ranking can provide a reference for the user to select the "spectral recipe". Further, after analyzing these massive data, we can get different indicators to provide users with reference. For example, in terms of different multispectral combinations of 4,000K color temperature, different usage orders can be made according to the user's gender, age, race, season, time, etc., so that the light environment platform constructed by the present invention can be used as other designers who are interested or willing to provide human centric spectral recipe, use these indicators for commercial services and operations. Therefore, the light environment platform constructed by the present invention can allow the intelligent human centric lighting system 100 to provide various usage experiences after curation or algorithm operation as the default multispectral combination. In addition, users can also choose a "spectral recipe" that is most selected by the user for lighting according to the user experience data after calculation.

In the embodiment of FIG. 4, step 450 can exist selectively, for example, if the user only establishes the database for user's own use, user can directly record and store the effective use experience in the external private cloud 6153 or public cloud 6155 after determining that it is valid in step 430 without this step 450. The database of the "spectral recipe" construction service to be constructed in step 450 will be described in the following embodiments.

Next, in FIG. 4, there is another embodiment that can be used for commercial services and operations, it can provide an authoring platform that allows different users or creators to create new "spectral recipe" through this authoring platform. As shown in step 460, a "spectral recipe" authoring platform is provided in the intelligent human centric lighting system 100. The client terminal 630 using this "spectral recipe" authoring platform can be distributed all over the world and can communicate with each other through the internet. The "light environment platform" connection in the cloud 610 of the present invention. Obviously, the present invention defines a "spectral recipe" creation platform here, that is, a "spectral recipe" creation platform means that a user or client terminal 630 can connect to the public cloud 6155 in the cloud 610 or a "sharing platform" through the internet, so that users or client terminal 630 can use the "spectral recipe" information on the public cloud 6155 or "sharing platform" for editing work. Therefore, after the user or client terminal 630 obtains various calculated usage experience data from the "sharing platform", the user or client terminal 630 can obtain the experience data based on the user's gender, age, race, season, time, etc., edit or create by client terminal 630 to construct an edited "spectral recipe" of multi-scene or multi-emotional multispectral combination.

Firstly, the first embodiment of the present invention uses the "spectral recipe" creation platform for commercial service and operation. For example, for the emotional stimulation result of 4,000K color temperature, the user or client terminal 630 can combine different light scenes through the "spectral recipe" creation platform. For example, the first paragraph of client terminal 630 selects the multi spectra combination of Maldives, the second paragraph is to choose the multispectral combination of Bali, and finally, the third paragraph ends with the multispectral combination on the beach of Monaco. In this way, after each segment is matched or configured with the spectral irradiation time, a new spectral combination of the multi-light scene can be formed. Finally, the spectral combination of the multi-light scene can be stored in the "sharing platform", which can provide other users with options. The spectral combination of this multi-light scene serves as the "spectral recipe" for its emotional adjustment. Among them, the creation platform of the present invention can also select a specific color temperature at a specific time, for example, when a user wants to perform emotional stimulation at 9:00 am, the user can further select the aforementioned three multispectral combinations at 9:00 am, further, the multispectral irradiation time of each segment can be configured to be the same or different, for example, each segment is irradiated for 15 minutes. The first stage and the third stage may be arranged for 15 minutes, and the second stage may be arranged and irradiated for 30 minutes, and these same or different time configurations can be selected by the user.

Secondly, in the second embodiment of the present invention using the "spectral recipe" creation platform, different color temperatures (that is, multiple emotions) can be combined to achieve specific emotional stimulation results through lighting with multiple emotions, for example, the client terminal 630 can use the "spectral recipe" creation platform to combine multiple emotions. For example, the first paragraph of the client terminal 630 is to select a multispectral combination of 4,000K (happy emotion), and the second paragraph is to select 3,000K (excited emotion). Finally, the third paragraph ends with a multispectral combination of 5,700K (amusement emotion). In this way, after each segment is matched or configured with multispectral irradiation time, a new multi-emotional multispectral combination can be formed. Finally, this multi-emotional multispectral combination can be stored in the "sharing platform", which can provide users with choices. This multispectral combination of multiple emotions serves as the "spectral recipe" for its emotional adjustment. Similarly, the creation platform in this embodiment can also select a specific color temperature at a specific time. For example, when the user wants to perform emotional stimulation at 9:00 am, user can further select the above three paragraphs spectral combination at 9:00 am. Further, the multispectral irradiation time of each segment can be configured to be the same or different, for example, each segment is irradiated for 15 minutes. The first stage and the third stage may be arranged for 15 minutes, and the second stage may be arranged and irradiated for 30 minutes, and these same or different time configurations can be selected by the user.

Next, it should be further explained that after the editing or creation of the above-mentioned first embodiment (multispectral combination of multi-light scenes) and the second embodiment (multispectral combination of multi-mood light scenes) is completed, step 430 also needs to go through step 430. Process to step 470. For example, step 411 should be passed first, and the illumination should be performed through the multi-spectrum adjusted by a plurality of LED lamps group 621 with different spectra. Next, after step 430, it is determined whether the combination of the above-mentioned "spectral recipe" achieves the effect that the creator wants, including: the spectral combination of the multi-light scene of the first embodiment and the irradiation time of the corresponding configuration, and the second embodiment the multi-emotional spectral combinations and configured exposure times. If the effect set by the creator can be achieved, the control parameters of the LED lamps group 621 required to construct these "spectral recipe" can be formed into a database that can provide a "spectral recipe" construction service, as shown in step 450. Then, as shown in step 470, after uploading the database of the "spectral recipe" construction service constructed in step 450 to the cloud, these "spectral recipe" can be added to the public cloud 6155 of the present invention to form a light environment platform. If after step 430, it is determined that a certain "spectral recipe" cannot achieve the effect set by the creator, then you can go back to step 411 to adjust the irradiation time of each segment, or change to a different light scene combination (the first embodiment) or change different emotional combinations (the second embodiment), until these "spectral recipe" can achieve the effect set by the creator, then the process from step 430 to step 470 can be used to judge that these are effective. The "spectral recipe" of the light environment is added to the public cloud 6155 of the present invention to form a light environment platform.

In addition, in order to make the multi-scene combination or multi-emotion combination of the "spectral recipe" creation platform effective, it may be necessary to go through a specific LED lamps group 621 or a specific configuration diagram to achieve the best effect. Therefore, the present invention is further configured with a database of hardware services, as shown in step 420, and further configured with a database of software services, as shown in step 440. Among them, the database of hardware services and the database of software services are also embedded with some management information when building "spectral recipe", including installation or delivery of hardware devices, or including providing and building these "spectral recipe" through the database of software services software services such as space design, scene planning, or interface setting required by spectral recipe. In addition, the database of the hardware service and the database of the software service may be configured at one end of the client terminal 630, or may be configured in the cloud 610, which is not limited in the present invention. Obviously, in the embodiment of FIG. 4, the present invention has provided the process of constructing various "spectral recipe" and the database of "spectral recipe" construction services, as well as the hardware services required for the construction of "spectral recipe". The database and software service database have been established in the light environment platform. It should be noted that the "sharing platform" finally established in step 470 is a "spectral recipe" that can provide effective spectral combinations of multi-light scenes and multi-emotional light scenes. "Sharing Platform" provides various commercial services and operations.

Figure 5A:
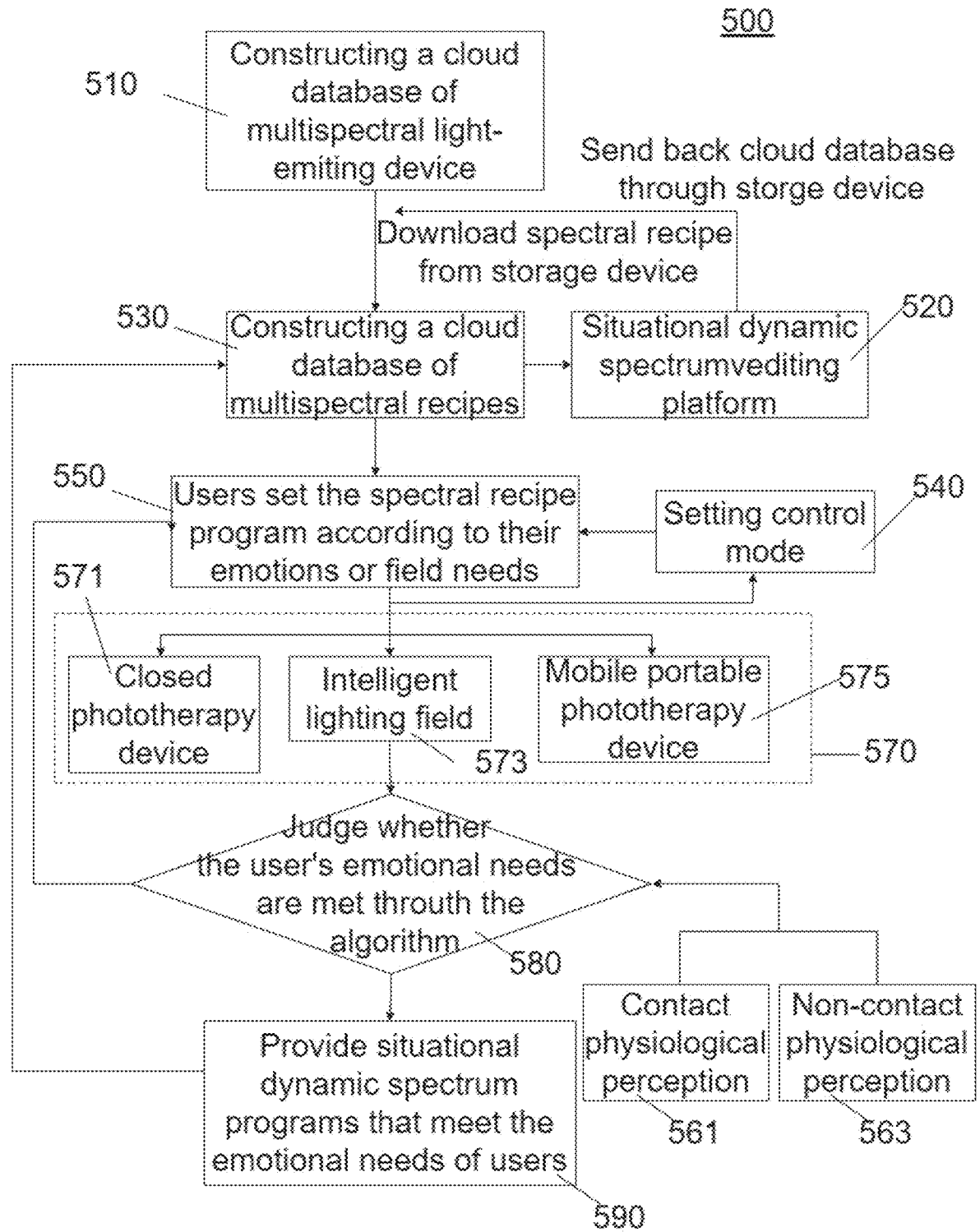
FIG. 5a is an automatically adjustable intelligent human centric lighting method of the present invention.

Next, please refer to FIG. 3 and FIG. 5a, FIG. 5a is an automatically adjustable intelligent human centric lighting method 500 of the present invention. First, as shown in step 510, the management control module 611 loads the "human centric lighting parameter database" stored in the memory module 617 into the management control module 611. Among them, the "human centric lighting parameter database" stored in the memory module 617 already knows that various color temperatures can give people (or users) corresponding emotional stimulation. For example, a specific color temperature can make a specific emotion have the stimulating effect of additive reaction.

Next, as shown in step 530, a cloud data database of multispectral recipe for human centric lighting is constructed. In step 530, the "spectral recipe" stored in the "sharing platform" established in step 470 can be downloaded by the management control module 611 as a cloud data database source for constructing a multispectral recipe with human centric lighting in the present invention. Therefore, the process of forming the "spectral recipe" established in step 470 will not be described in detail, please refer to the detailed description of step 470.

Next, as shown in step 520, a "situational dynamic spectrum editing platform" is provided. Similarly, the present invention defines a "situational dynamic spectrum editing platform" here, which is similar to the aforementioned "spectral recipe creation platform". The client terminal 630 can connect to the public cloud 6155 or "sharing platform" in the cloud 610 via the internet, so that the user or client terminal 630 can use the "spectral recipe" information on the public cloud 6155 or "sharing platform" for situational editing work. After the "situational dynamic spectral editing platform" obtains a variety of "spectral recipe" data from the "sharing platform", the "situational dynamic spectral editing platform" can edit or create the "spectral recipe" through the software application to construct an edited "situational dynamic spectrum program" that achieves (or satisfies) a specific emotional effect. This "situational dynamic spectrum program" can also be uploaded to the external private cloud 6153 in the cloud 610 and public cloud 6155, forming a database of "situational dynamic spectrum programs" that achieve (or satisfy) specific emotional effects.

Next, the editing process of the "situational dynamic spectrum program" in step 520 is described in detail. Please refer to FIG. 5b, which shows the editing process of the situational dynamic spectrum editing platform of the present invention. As shown in step 5210, the client terminal 630 downloads the "spectral recipe" stored in the "sharing platform" established in step 470 to the editing device used by the client terminal 630 through the internet to the management control module 611 in the cloud 610, for example, the editing device can be a computer or a smartphone or a workstation, one or more "spectral recipe" is connected to the software as a service (SaaS) or platform as a service (PaaS) configured in the cloud 610 through the editing device of the client terminal 630in the system, afterwards, as shown in step 5220, through the SaaS or PaaS system configured on the cloud, set the lighting parameters of a specific color temperature (that is, a specific mood) for the downloaded "spectral recipe", wherein the setting items of the lighting parameters include the generation time of the spectrum, the latitude and longitude of the spectrum, the brightness of the spectrum, the contrast of the spectrum, the flicker rate of the spectrum, etc., can be adjusted and set, and the above-mentioned adjustment methods are the same as the aforementioned methods of the present invention, including, replacing the "spectral recipe" in order of light scenes, or replace the light scene in the "spectral recipe", or delete a specific light scene in the "spectral recipe", or add a new light scene in the "spectral recipe", etc., because these adjustment methods are all has already been explained, so it will not be repeated here, for example, when the user downloads a spectral combination of a multi-light scene as the "spectral recipe" for emotional adjustment of happiness (4,000K), the multispectral brightness and the multispectral contrast can be finely adjusted, and the spectral flicker rate in the second-stage Bali multispectral combination can also be adjusted at the same time, and the lighting sequence or lighting time of the aforementioned three-stage multispectral combination can also be adjusted or consider the latitude and longitude of the spectrum or the multispectral combination provided by the time of day, for example, add a multispectral combination at 4,000K color temperature in Cannes, France, or delete the beach in Monaco through a SaaS or PaaS system. The multispectral combination above is changed to the multispectral combination at 4,000K color temperature in Miami Beach, USA. For example, when the user or client terminal 630 downloads a "spectral recipe" for a spectral combination of a multi-light scene and uses the SaaS or PaaS system to perform the combination of other light scenes, the above adjustment and change process can also go to step 510 The "human centric lighting parameter database" stored in the memory module 617 is used to combine other emotions (color temperature). The color temperature of the serene mood of the segment is used as the end stage of the lighting.

Next, as shown in step 5230, the relationship between the context function and the "spectral recipe" is edited. In step 5230, the "spectral recipe" that has been adjusted or set in step 5220 is edited in relation to the specific context function that the user or client terminal 630 wants to achieve, wherein, the relationship is divide the specific situational function you want to achieve into multiple blocks, and each of these blocks corresponds to a light scene in the "spectral recipe", for example, in step 5210, the user downloads a "spectral recipe" for a happy, excited and amusement multi-light scene, and when the user or client terminal 630 finally wants to achieve a good situational effect in the conference room (wherein, the so-called good conference situation effect, for example, the client terminal 630 chooses to be in the conference process, hoping that all the participants can stay relaxed at the beginning, stay focused during the discussion, and stay happy at the conclusion). The original "spectral recipe" can be adjusted to the "spectral recipe" of multi-light scenes such as relaxation, concentration and amusement through step 5220, and in step 5230, the user or client terminal 630 divides the meeting process into openings, discussing and conclusion three situational blocks, and then, the three situational blocks of opening, discussion and conclusion are corresponding to the "spectral recipe" of multi-light scenes of relaxation, concentration and amusement, so that the whole meeting can be The context of the process is linked to the "spectral recipe" of the multi-light scene in the conference room. Next, as shown in step 5240, after the user or client terminal 630 completes the "spectral recipe" correlation between the context of the conference process and the multi-light scene, and then adds "time setting" to the context block, it can complete a "situational dynamic spectrum program" with the function of conference situation, for example, setting the time for the opening, discussing and conclusion of the meeting to 5 minutes, 15 minutes and 10 minutes, as shown in FIG. 5c, can complete the "situational dynamic spectrum program with meeting context function". Obviously, the "situational dynamic spectrum program" obtained through the editing process in FIG. 5b can be stored in the memory module 617 or the external private cloud 6153 or the public cloud 6155 through step 530. Afterwards, these "situational dynamic spectrum programs" stored in the external private cloud 6153 can be provided for their own use as "situational dynamic spectrum programs" with automatically adjustable and intelligent human centric lighting, for example, when the user or client terminal 630 chooses to use a conference "situational dynamic spectrum program", the spectrum in the conference room can be automatically adjusted during the conference. Of course, the conference "situation dynamic spectrum program" edited by the client terminal 630 can also be stored in the public cloud 6155, so that business activities that are opened to other users through the cloud 610 can be achieved. Obviously, at this time, in step 530, in addition to the various "spectral recipe" downloaded from step 470, it also includes "situational dynamic spectrum programs", therefore, it can be stored in the cloud database established in step 530. Provide users with human centric lighting. In addition, it should be emphasized that in this embodiment, the editing of the "situational dynamic spectrum program" of multi-light scenes includes a combination of multi-light scenes with a single emotion and a combination of multi-light scenes with multiple emotions. Of course, it also includes the specific emotions in the multi-light scene combination can also be combined using the multi-light scene, which is not limited in the present invention.

Figure 5B:
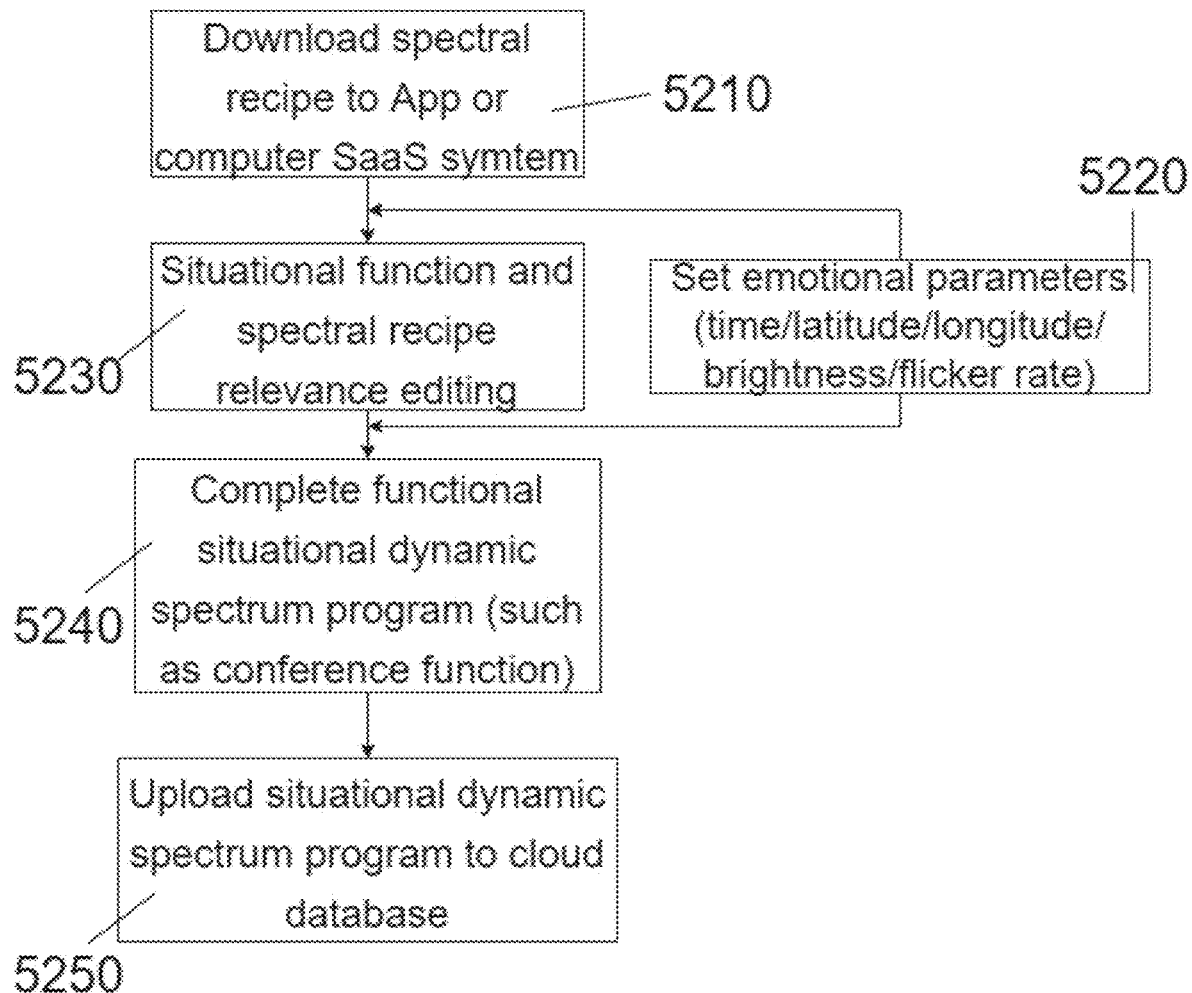
FIG. 5b is an editing process of the situational dynamic spectrum editing platform of the present invention.
Figure 5C:
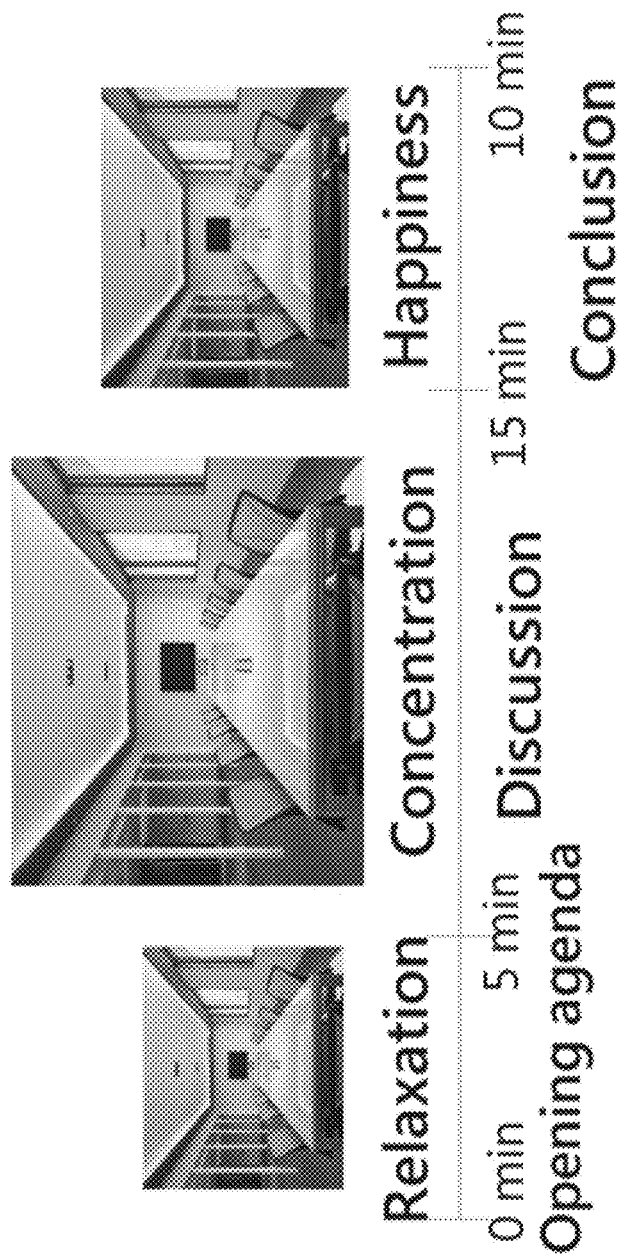
FIG. 5c is a kind of situational dynamic spectrum program with conference function of the present invention.

In addition, in the editing process of FIG. 5b above, another embodiment can also be selected, that is, the client terminal 630 downloads the "spectral recipe" stored in the "sharing platform" established in step 470 to the editing device used by the client terminal 630 through the internet to the management control module 611 in the cloud 610, and then, the user or client terminal 630 can select to edit the desired special situation setting function through SaaS or PaaS system (that is, first distinguish multiple blocks of specific situation functions), and then associate the desired special situation setting with the downloaded "human centric lighting parameter database", so as to complete the correlation editing between multiple situation blocks and corresponding emotions (color temperature), so as to form a multi emotional multi light scene combination, for example, the editor has first divided the meeting process into three blocks: opening, discussing and conclusion, and then went to the "human centric lighting parameter database" stored in the memory module 617 to select the "spectral recipe" corresponding to the multi light scene formed by the corresponding emotions such as relaxation, concentration and amusement, or select the corresponding amusement "spectral recipe" for focused and relaxed multi light scenes. Since the way of travel relevance editing is the same, it will not be repeated in this embodiment.

Next, the present invention provides another preferred embodiment of an automatically adjustable intelligent human centric lighting method. Since the "situational dynamic spectrum program" constructed in step 530 is the result obtained by editing by individual client terminals 630, in order to achieve better effects, it is necessary to consider the light stimulation effects of different users on the "spectral recipe", and/or need to consider whether the lighting hardware configuration in different fields can achieve the light stimulation effect of "spectral recipe", which need to be adjusted.

Next, as shown in steps 550 and 570, the user or editor adjusts the "spectral recipe" in the "situational dynamic spectrum program" in order to meet emotional needs. First, the user or client terminal 630 has downloaded a "situational dynamic spectrum program" from the external private cloud 6153 or public cloud 6155, and this "situational dynamic spectrum program" can be a "spectral recipe" for a multi-emotional and multi-light scene, or a "spectral recipe" for a multi-light scene with a single emotion. Next, the user or client terminal 630 needs to be in a "specific environment" to execute the selected "situational dynamic spectrum program", wherein, in the embodiment of the present invention, the "specific environment" is divided into three types. The aspect, as shown in step 570, includes: a closed lighting system, an intelligent lighting field, and a portable human centric lighting device. When the "specific environment" is a closed lighting system, wherein the closed lighting system is a closed control room with multiple light-emitting devices (for example, a closed cavity that can isolate external light), it can It is provided that one or more users can receive the selected "situational dynamic spectrum program" in the closed cavity to perform the "spectral recipe" irradiation, as shown in step 571. In the process of spectral lighting, the present invention provides a function with control mode setting. For example, the multi-light scene can be controlled by the App on the mobile device used by the user or the client terminal 630 or the control module in the closed cavity, for example, under the influence of an environment with ambient light, the "spectral recipe" can be adjusted for the selected "situational dynamic spectrum program". The adjustment methods include time/longitude/latitude/brightness/flashing rate, etc., as shown in step 540. In addition, when the "specific environment" is an intelligent lighting field, the intelligent lighting field is a field with multiple light-emitting devices that can accommodate multiple people, such as a conference room, a classroom, a kind of office place, a kind of social place, or a kind of factory, etc., so that multiple users can receive the "situational dynamic spectrum program" in the intelligent lighting field to perform "spectral recipe" lighting, as shown in step 573. In the process of spectral illumination, the controller, user or client terminal 630 of the field can control the selected "situational dynamic" through the application (App) on the mobile device used or the control module in the field "spectral program" to adjust "spectral recipe", for example, under the influence of an ambient light environment, or under the influence of the number of people in the field, to adjust the "spectral recipe", the adjustment methods include, time/latitude/longitude/brightness/flashing rate, etc., as shown in step 540. And, when the "specific environment" is a mobile portable lighting device, the mobile portable human centric lighting device is a virtual device related to the metaverse, such as: virtual reality (VR), mixed reality (MX) or an extended reality (XR) device, the user can accept the selected "situational dynamic spectrum program" through the virtual device to perform the "spectral recipe" irradiation, as shown in step 575. In the process of spectral illumination, the user or client terminal 630 can adjust the "spectral recipe" through the App on the mobile device or the control module in the virtual device, for example, in an environment with ambient light. Under the influence, the "spectral recipe" can be adjusted for the selected "situational dynamic spectrum program", and the adjustment methods include time/latitude/longitude/brightness/flashing rate, etc., as shown in step 540.

Figure 6:
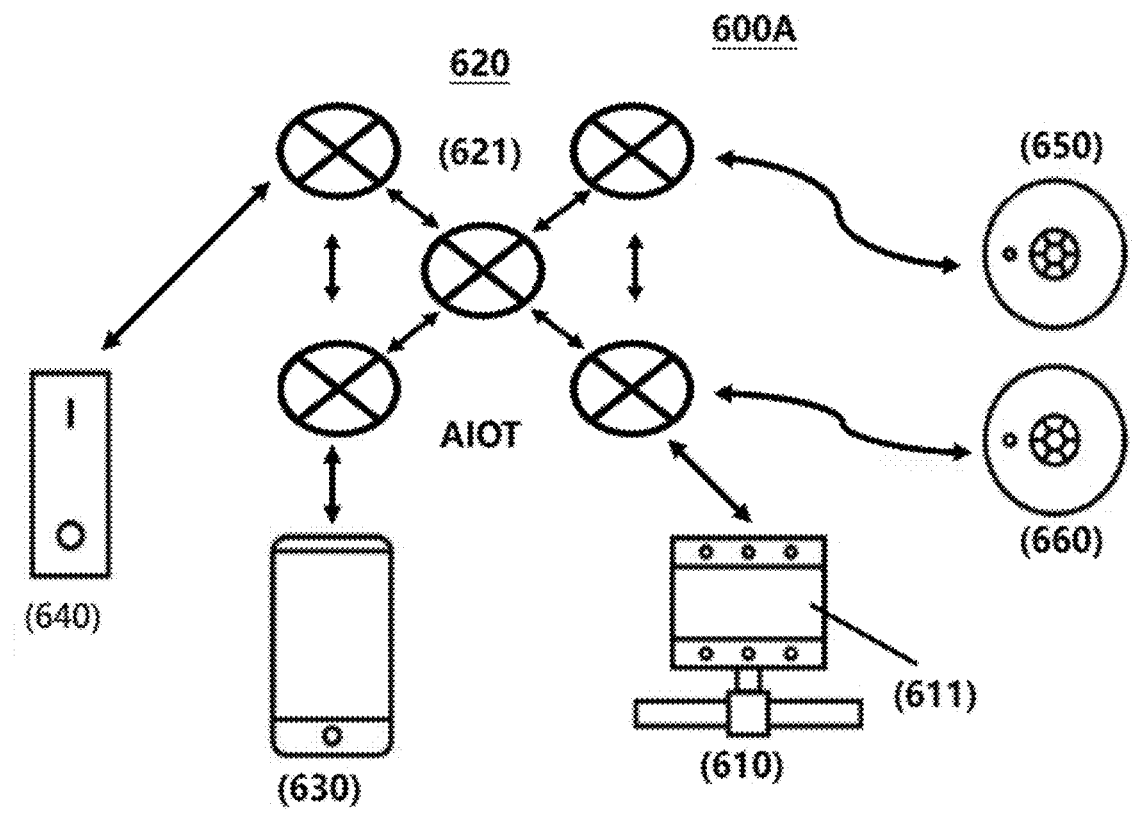
FIG. 6 is an intelligent human centric light system applied to commercial operation of the present invention.

During the operation of the above steps 540, 550 and 570, it is obvious that the default value of the "spectral recipe" is adjusted for the "specific environment" where the user is located. In the process of performing this default value adjustment, the ambient light information can be transmitted to the user or the user through the wireless communication device through the ambient light sensor 650 (as shown in FIG. 3 or FIG. 6) set in the "specific environment". It is an application (App) on the mobile device of the client terminal 630 or a control module in the "specific environment", which is used as a reference for adjusting the default value of the "spectral recipe". In addition, the occupancy sensor 660 (as shown in FIG. 3 or FIG. 6) set in the "specific environment" can also transmit the information of the number of people in the environment to the mobile device of the user or client terminal 630 through the wireless communication device. The occupancy sensor 660 can be a vibration sensor, and the frequency of vibration can be used to determine the number of people The occupancy sensor 660 may also be a temperature sensor, and the number of people is judged by the ambient temperature. In addition, the occupancy sensor 660 may also be a camera system, which judges the number of people through artificial intelligence (AI) face recognition. In addition, the occupancy sensor 660 can also be a gas concentration detector for detecting changes in the concentration of oxygen ($O_2$) or carbon dioxide ($CO_2$), to judge the effect of the user's spectral irradiation. When the temperature increases and the carbon dioxide ($CO_2$) concentration also increases, it is judged that the spectral irradiation achieves the desired emotional effect. Obviously, through the operation of step 540, step 550 and step 570, a "situational dynamic spectrum program" that can be automatically adjusted for intelligent human centric lighting can be formed.

The present invention then provides another preferred embodiment of an automatically adjustable intelligent human centric lighting method. It is to further provide some sensing devices to feedback whether the user achieves the required emotional effect after being irradiated by the "spectral recipe" of the "situational dynamic spectrum program". These sensing devices include contact physiological sensors (e.g., step 561) or non-contact optical sensors (e.g., step 563). Among them, the contact type physiological sensor is configured on each user to measure the user's heartbeat, blood pressure, pulse, blood oxygen concentration or electrocardiogram, etc., to determine whether the user meets the required emotion. The non-contact optical sensor can be configured in the light environment where the user is located to measure the illuminance, color temperature, spectrum, color rendering index, etc.

As shown in step 580, after the user has performed the "spectral recipe" of the specific "situational dynamic spectrum program" in the "specific environment", an algorithm will be used to determine whether the current spectral irradiation process has reached the user's mood need. Wherein, the algorithm in step 580 may be a ratio of the signals between the user's physiological signals (including: heartbeat, blood pressure, pulse and respiration rate) obtained through an algorithm, and this ratio is used to determine whether the specific emotional needs are met. Therefore, after the calculation processing of the management control module 611, a database of physiological signal ratios relative to various emotions is established and stored in the memory module 617 in the cloud 610 or the internal private cloud 6151. For example, when the user is illuminated by the "situational dynamic spectrum program" of happy emotions for a period, the heartbeat, blood pressure and blood oxygen are getting back to the App on the mobile device or the "specific environment" through the contact physiological sensor in step 561. At this time, the App on the mobile device or the control module in the "specific environment" calculates a proportional value from the feedback data through an algorithm, and then transmits this proportional value to the management control module 611 through the internet, compare the ratio value stored in the memory module 617 or the internal private cloud 6151 through the management control module 611. For example, if the ratio value calculated by the algorithm falls between 1.1 to 1.15, and the management control module 611 determines that the probability of this ratio value reaching a happy mood is 80%, and the probability of reaching a happy mood is 20%. If we judge whether the probability of achieving the effect is 75%, the management control module 611 will judge that the user has reached the required happiness after lighting through the "spectral recipe" of the selected "situational dynamic spectrum program" and will stop the irradiation program after the "situational dynamic spectrum program" completes the irradiation program. Then, in step 590, the "spectral recipe" data of the current "situational dynamic spectrum program" is stored in the internal private cloud 6151, the external private cloud 6153 or the public cloud 6155 in the cloud 610. If it is judged that after the user is illuminated by the "spectral recipe" of the selected "situational dynamic spectrum program", the ratio value calculated by the algorithm has only a 50% probability of reaching the happy mood, which means that the happy mood required by the user has not yet been achieved. Currently, it is necessary to return to step 550, after adjusting the "spectral recipe" of the selected "situational dynamic spectrum program" through the control mode of step 540, perform the lighting program again, and pass the contact method of step 561. The physiological sensor gets back the user's heartbeat, blood pressure and blood oxygen to the App on the mobile device or the control module in the field after the ratio calculated by the algorithm, and then transmits the ratio to the cloud database through the internet at a time and communicates with the cloud. The proportions in the database are compared until the desired happiness emotion is reached. Obviously, in the storage process of step 590, it will also be stored in step 530 at the same time, so at this time, in the cloud database established in step 530. In addition to the various "spectral recipe" downloaded from step 470, it also includes the "situational dynamic spectrum program" adjusted by the algorithm. Therefore, storing in the cloud database of the "situation dynamic spectrum program" established in step 530 can provide a more effective "situation dynamic spectrum program" for the user to perform human centric lighting. In addition, it should be emphasized that in this embodiment, the editing of the "situational dynamic spectrum program" of multi-light scenes includes a combination of multi-light scenes with a single emotion and a combination of multi-light scenes with multiple emotions. Of course, it also includes the specific emotions in the multi-light scene combination can also be combined using the multi-light scene, which is not limited in the present invention.

The intelligent human centric lighting system or method provided by the present invention can judge whether the user can judge or feel whether the effect has been achieved after the illumination of the "spectral recipe" selected by the user through the feedback signal. The solution provided by the present invention is to judge through the user's actual physiological signal. Therefore, the above embodiment of using physiological signals as an algorithm is only an example to let the public know the implementation of the technical means of the present invention, so it should not be a limiting condition of the present invention within the scope of rights. The invention should emphasize that the scope of the "algorithm" of the present invention is if the individual comparison is carried out through the user's physiological signals, or the data in the cloud 610 database is further compared after processing the physiological signals.

According to the above-mentioned intelligent human centric lighting method that can be automatically adjusted, the present invention further provides an intelligent human centric lighting system for commercial operation, as shown in FIG. 6. The intelligent human centric lighting system 100 for commercial operation of the present invention includes: a cloud 610, a management control module 611, a lighting field terminal 620 for intelligent lighting, and a client terminal 630. The devices configured in the lighting field terminal 620 include: a light-emitting device or LED lamps group 621, at least one occupancy sensor 660, at least one ambient light sensor 623, and a switch device 640. The lighting field terminal 620 includes a "specific environment". According to FIG. 5*a*, the "specific environment" can be divided into three fields, including: a closed space that can be used by multiple people or an intelligent lighting field domain, as well as mobile portable human centric lighting devices for personal use or enclosed spaces.

First, FIG. 6 discloses an intelligent human centric lighting system 600A for commercial operation, which can be applied to an embodiment used by multiple people. The client can use the portable communication device to download the "spectral recipe" or "situational dynamic spectrum program" to the cloud 610 through the internet and use the portable communication device to activate the LED lamps group 621 for human centric lighting, in order to form an intelligent human centric lighting system that can be automatically adjusted. Wherein, in this embodiment, the client may be at the remote end, or may be at the specific environment end at the near end. When the client is remote, the internet is the Artificial Intelligence of Things (AIoT) formed by the Internet of Things (IoT) and Artificial Intelligence (AI). When the client is at the near end, the internet is a wireless communication protocol formed by a gateway, including Wi-Fi or Bluetooth.

When a plurality of users has been distributed in a closed space or intelligent lighting field, the portable communication device can carry out specific "spectral recipe" or "situational dynamic spectrum program" human centric lighting for the starting LED lamps group 621. The closed lighting system is a closed space with a plurality of light-emitting devices (for example, a closed cavity that can isolate external light), which can provide one or more users to receive human centric lighting in the closed cavity. The intelligent lighting field is a field with multiple light-emitting devices that can accommodate multiple people, such as a conference room, a classroom, an office, a social place or a factory, which can provide multiple users to receive human centric lighting in the intelligent lighting field.

In addition, the LED lamps group 621 can be further configured in a closed space or in an intelligent lighting field. When multiple users perform human centric lighting in the closed space, the closed space can provide a space that is isolated from external environmental interference, allowing users to immerse themselves in the selected "spectral recipe" or "situational dynamic spectrum program". At the same time, in order to enable people to achieve the desired effect faster due to lighting, the contact physiological sensor configured on each user can also be used to measure the user's heartbeat, blood pressure, pulse, blood oxygen concentration or electrocardiogram, etc., to determine whether the user has achieved the required emotion. In addition, face recognition can also be performed through the vibration frequency, ambient temperature, ambient carbon dioxide concentration detected by the occupancy sensor 660 and the background ambient light sensor 650 configured in the intelligent lighting field, and the ambient carbon dioxide concentration, spectrum, The light intensity, flashing rate, and color temperature are transmitted to the management control module 611 in the cloud 610 through the Artificial Intelligence of Things (AIoT) for calculation, so as to determine whether the user has achieved the set effect. Similarly, in the process of spectral illumination, the "spectral recipe" of the multi-light scene can be adjusted through the App on the mobile device used by the client terminal 630 or the control module in the intelligent lighting field, for example, when the ambient light sensor When the 650 detects the influence of ambient light, it can adjust the "spectral recipe" of the selected "situational dynamic spectrum program". The adjustment methods include time, latitude and longitude, brightness, flashing rate, etc. show the operation process of step 540, step 550, step 570 and step 580).

Next, FIG. 6 further discloses an embodiment of an intelligent human centric lighting system 600A for commercial operation as shown, applied to personal use. The user can use the portable communication device to download the "spectral recipe" or "situation dynamic spectrum program" to the cloud 610 through the internet and activate the mobile portable human centric lighting device through the portable communication device to perform human activities. Due to lighting, to form an intelligent human centric lighting system that can be automatically adjusted. Especially when the user has worn the portable human centric lighting device on the user's eyes, the portable communication device can be used to activate the LED lamps group 621 configured in the portable human centric lighting device. A specific "spectral recipe" or "situational dynamic spectrum program" for human centric lighting. Wherein, the portable human centric lighting device is a virtual device related to the metaverse, such as a Virtual Reality (VR), Mixed Reality (MX) or Extended Reality (XR) device, which can provide a single user receives human centric lighting through a virtual device.

In addition, in order to enable the human centric lighting of the mobile portable human centric lighting device to achieve the desired effect faster, the contact type physiological sensor configured on the user's body can also be used to measure the user's heartbeat, blood pressure, pulse, blood oxygen concentration or electrocardiogram, etc., to determine whether the user has the required emotion. Similarly, in the process of spectral irradiation, the "spectral recipe" of the multi-light scene can be adjusted through the App on the mobile device used by the client terminal 630 or the control module in the closed cavity (for details, please refer to step 540, step 550, step 570 and step 580 during the operation).

In a preferred embodiment, the configuration of the LED lamps group 621 can be configured according to the customized requirements through the hardware service database of step 420 and the software service database of step 440. Finally, the portable communication device in the automatic adjustable intelligent human centric lighting system of the present invention can be an intelligent phone, a tablet device or a workstation. The portable communication device can download an application (APP) containing intelligent human centric lighting from the Artificial Intelligence of Things (AIoT) to the management control module 611. Through this app, the user can connect with the public cloud in the cloud 610, and then select the desired "spectral recipe" or "dynamic spectrum program" from the public cloud for human centric lighting. At the same time, through this app, the LED lamps group 621 can also be remotely turned on or off through the short-range communication protocol, to control the spectrum to achieve the effect of human centric lighting. Among them, if the user confirms that those "spectral recipe" or "situational dynamic spectrum programs" are effective, he can download these "spectral recipe" or "situational dynamic spectrum programs" to the portable communication device of the client, and then configure the switching device 640 of the client, You can directly open the "spectral recipe" or "situational dynamic spectrum program" for human centric lighting without internet connection, which allows users to quickly enter the human centric lighting program.

The above-mentioned intelligent human centric lighting system that can be adjusted automatically is to establish a database of the brain's "blood oxygen-level dependent response increase" condition through the intelligent human centric lighting system. After the database is edited by the spectral recipe, a cloud database of multispectral light-emitting devices is constructed. The cloud database can provide users to set the emotional needs of the brain to be achieved in the intelligent human centric lighting system, and the intelligent human centric lighting system can judge or suggest the operation logic of the light distribution equation. Lighting field and movable human centric lighting device. After that, when the user experiences the light situation, the intelligent human centric lighting system algorithm is used to determine the user's physiological and psychological state. If the emotional needs of the brain have not been fulfilled, the "spectral recipe" program will be continuously modified through the feedback signal of the wireless device, and after re-adjusting the "spectral recipe", it will be re-verified whether the expected emotional needs have been met. If the brain reaches the emotional needs, it will provide a "spectral recipe" or "situational dynamic spectrum program" formed by lighting that meets the user's emotional needs to carry out the lighting process. Obviously, the intelligent human centric lighting method and system disclosed by the present invention can make the human centric lighting effect of the emotional needs of the brain can be commercialized and benefit more users without the need to use fMRI.

Finally, it should be emphasized once that the above is only a better embodiment of the present invention and is not used to limit the scope of the rights of the present invention. At the same time, the above description should be clear to and implemented by those with general knowledge in the relevant technical field. Therefore, other equivalent changes or modifications not separated from the concept disclosed in the present invention should be included in the scope of patent claims of the present invention.

What is claimed is:

1. A grading method for establishing a physiological emotional response and an electroencephalograph through a human-centric lighting system and an electroencephalograph (EEG) device, comprising:
   obtaining an enhanced spectrum of different emotions, wherein the enhanced spectrum is a specific color temperature that has a multiplying effect on the specific physiological emotional response identified by a fMRI, further comprising:
   participants viewing emotion-inducing images in the fMRI;
   recording various emotional brain hyperemia reactions of participants after being stimulated by the images through the fMRI;
   providing spectrum with different color temperatures through lighting;
   recording various emotional brain hyperemia reactions of the participants after being stimulated by the lighting through the fMRI;
   screening specific color temperatures that can increase the brain hyperemia reaction with the specific physiological emotions; and
   obtaining the enhanced spectrum corresponding to the specific physiological emotions by achieving brain hyperemia reactions with specific color temperatures;
   inducing specific physiological emotions of new participants by wearing the EEG device and providing an element with specific emotional stimuli to stimulate the specific physiological emotions in the new participants;
   after the inducing step, performing a lighting program by activating the human-centric lighting system to provide lighting with the different color temperatures to the new participants, and recording and storing EEG files under different color temperatures for the specific physiological emotions;
   classifying the EEG files for the specific physiological emotions by using transfer learning model based on the similarity of the enhanced spectrum with the different color temperatures, wherein the EEG files are grouped according different color temperatures and ranked bases on their similarity; and the most similar EEG file is considered the 'target value' with the strongest emotion, while the least similar is considered the 'initial value' with the weakest emotion; and
   establishing an EEG grading database by sorting the EEG files of various specific color temperatures based on their similarity.

2. The method of claim 1, wherein the different color temperatures are formed by adjusting lighting parameters.

3. The method of claim 2, wherein the lighting parameters may include spectrum, intensity, frequency of twinkling or color temperature of the lights.

4. The method of claim 1, wherein the element which has the specific physiological stimulation to the new participants further includes pictures or videos.

* * * * *